US008038996B2

(12) United States Patent
Mahadevan

(10) Patent No.: US 8,038,996 B2
(45) Date of Patent: Oct. 18, 2011

(54) COMPOSITION AND METHOD FOR CANCER TREATMENT

(75) Inventor: Daruka Mahadevan, Tucson, AZ (US)

(73) Assignee: University of Arizona, Tucson, AZ (US)

(*) Notice: Subject to any disclaimer, the term of this patent is extended or adjusted under 35 U.S.C. 154(b) by 375 days.

(21) Appl. No.: 11/075,891

(22) Filed: Mar. 10, 2005

(65) Prior Publication Data
US 2006/0088521 A1 Apr. 27, 2006

Related U.S. Application Data

(60) Provisional application No. 60/557,258, filed on Mar. 27, 2004.

(51) Int. Cl.
A61K 39/395 (2006.01)
C07K 14/705 (2006.01)
(52) U.S. Cl. ............... 424/143.1; 424/130.1; 424/133.1; 424/135.1; 424/138.1; 424/141.1; 424/152.1; 424/155.1; 424/156.1; 424/172.1; 424/174.1
(58) Field of Classification Search ............... 424/130.1, 424/133.1, 135.1, 138.1, 141.1, 143.1, 144.1, 424/155.1, 156.1, 174.1, 152.1, 172.1
See application file for complete search history.

(56) References Cited

U.S. PATENT DOCUMENTS

| 5,593,847 | A | 1/1997 | Barnett et al. | |
| 6,297,053 | B1* | 10/2001 | Stemmer | 435/440 |
| 6,759,045 | B2* | 7/2004 | Goldenberg et al. | 424/153.1 |
| 2002/0022031 | A1 | 2/2002 | Goldenberg et al. | |
| 2006/0024314 | A1 | 2/2006 | Stanners et al. | |

FOREIGN PATENT DOCUMENTS

| JP | 2004-505994 A | 2/2004 |
| WO | WO 02/12347 A1 | 2/2002 |
| WO | WO 03/068983 | 8/2003 |
| WO | WO 2004/092735 | 10/2004 |
| WO | WO 2005/073720 | 8/2005 |

OTHER PUBLICATIONS

Mittal.B.B.et.al. Cancer. 78: 1861-1870, 1996.*
Buchmann.I.et.al. Cancer Biotherapy and Radiopharmaceuticals. 17: 151-163, 2002.*
Cersosimo,R.J. Am.J.health-syst pharm, 60:Part 1: 1531-1548 and part II: 1631-1641, 2003.*
Ilantzis, C. et al., Neoplasia, 4(2): 151-163, 2002.*
Ueno, A., et al., Med. Bull. Fukuoka Univ., 29(2): 83-93, 2002.*
Alexis Biochemicals Newsletter, "Topix Latest Product Additions", Issue 2. Fall 2004, pp. 1-8.
S. Holloway, et al., "A Clinically Relevant Model of Human Pancreatic Adenocarcinoma Identifies Patterns of Metastasis Associated with Alterations of the TGF-β/Smad4 Signaling Pathway", International Journal of Gastrointestinal Cancer, vol. 33, No. 1, pp. 61-69, 2003.

H. Han, et al., "Identification of Differentially Expressed Genes in Pancreatic Cancer Cells Using cDNA Microarray", Cancer Research 62, pp. 2890-2896, May 15. 2002.
W. Pearson, "Flexible Sequence Similarity Searching with the FASTA3 Program Package", Methods in Molecular Biology, vol. 132: Bioinformatics Methods and Protocols, p. 185, 1999.
A. Pluckthun, et al., "Producing Antibodies in Escherichia coli: From PCR to Fermentation", Antibody Engineering: A Practical Approach. IRL Press, Oxford, 1996. pp. 203-252.
V. Hoff, et al., "New Developments in the Treatment of Patients with Pancreatic Cancer", Clinical Oncology Updates, 2001, vol. 4, No. 4, pp. 1-15.
H. Lynch, et al., "Familial Pancreatic Cancer: A Review", Seminars Oncology, vol. 23, No. 2, Apr. 1996, pp. 251-275.
E. Jaffee, et al., "Focus on Pancreas Cancer", Cancer Cell, 2002, vol. 2, No. 1, pp. 25-28.
N. Bardeesy, et al., "Pancreatic Cancer Biology and Genetics", Nature Reviews Cancer, 2002, vol. 2, No. 12, pp. 897-909.
A. Cubilia, et al., "Morphological Patterns of Primary Nonendocrine Human Pancreas Carcinoma[1]", Cancer Research, 1975, vol. 35, No. 8, pp. 2234-2248.
W. Klein, et al., "Direct Correlation Between Proliferative Activity and Dysplasia in Pancreatic Intraepithelial Neoplasia (PanIN): Additional Evidence for a Recently Proposed Model of Progression", Modern Pathology, 2002, .vol. 15, No. 4, pp. 441-447.
C. Iacobuzio-Donahue, et al., "Exploring the Host Desmoplastic Response to Pancreatic Carcinoma", American Journal of Pathology. vol. 160, No. 1, Jan. 2002. pp. 91-99.
M. Löhr, et al., "Transforming Growth Factor-β1 Induces Desmoplasia in an Experimental Model of Human Pancreatic Carcionoma[1]", Cancer Research, 2001, vol. 61, No. 2, pp. 550-555.
J. Gardner-Thorpe, et al., "Differential Display of Expressed Genes in Pancreatic Cancer Cells", Biochemical and Biophysical Research Communications, 2002. vol. 293, No. 1, pp. 391-395.
H. Friess, et al., "Microarrary-Based Identification of Differentially Expressed Growth-and Metastasis-Associated Genes in Pancreatic Cancer", Cellular and Molecular Life Sciences, 2003, vol. 60, No. 6, pp. 1180-1199.
B. Ryu, et al., "Relationships and Differentially Expressed Genes Among Pancreatic Cancers Examined by Large-Scale Serial Analysis of Gene Expression[1]", Cancer Research, Feb. 1, 2002, vol. 62, No. 3, pp. 819-826.
C. Iacobuzio-Donahue, et al., "Exploration of Global Gene Expression Patterns in Pancreatic Adenocarcinoma Using cDNA Microarrays", American Journal of Pathology, vol. 162, No. 4, Apr. 2003, pp. 1151-1162.
V. Smit, et al., "KRAS Codon 12 Mutations Occur Very Frequently in Pancreatic Adenocarcinomas", Nucleic Acids Research, vol. 16, No. 16, 1988, pp. 7773-7782.

(Continued)

Primary Examiner — Misook Yu
Assistant Examiner — Anne Holleran
(74) Attorney, Agent, or Firm — Oblon, Spivak, McClelland, Maier & Neustadt, L.L.P.

(57) ABSTRACT

Anti-CEACAM6 antibodies and antibody fragments, nucleic acids encoding them, methods of their manufacture, and methods to treat cancer using these compounds are provided.

20 Claims, 11 Drawing Sheets

OTHER PUBLICATIONS

C. Griffin, et al., "Consistent Chromosome Abnormalities in Adenocarcinoma of the Pancreas[1]", Cancer Research, 1995, vol. 55, No. 11, pp. 2394-2399.

K. Aoki, et al., "Suppression of Ki-ras p21 Levels Leading to Growth Inhibition of Pancreatic Cancer Cell Lines With Ki-ras Mutation But Not Those Without Ki-ras Mutation", Molecular Carcinogenesis, 1997, vol. 20, pp. 251-258.

N. Ikeda, et al., "The Association of K-ras Gene Mutation and Vascular Endothelial Growth Factor Gene Expression in Pancreatic Carcinoma", Cancer, Aug. 1, 2001, vol. 92, No. 3, pp. 488-499.

M. Wagner, et al., "A Murine Tumor Progression Model for Pancreatic Cancer Recapitulating the Genetic Alterations of the Human Disease", Genes Development, 2001, vol. 15, pp. 286-293.

R. Sotilo, et al, et al., "Wide Spectrum of Tumors in Knock-In mice Carrying a Cdk4 Protein Insensitive to INK4 Inhibitors", The EMBO Journal, 2001, vol. 20, No. 23, pp. 6637-6647.

N. Beauchemin, et al., "Nomenclature Announcement, Redefined Nomenclature for Members of the Carinoembryonic Antigen Family[1]", Experimental Cell Research, 1999, vol. 252, No. 2, pp. 243-249.

M. Kuroki, et al., "Identification and Comparison of Residues Critical for Cell-Adhesion Activities of Two Neutrophil CD66 Antigens, CEACAM6 and CEACAM8", 2001, vol. 70, No. 4, pp. 543-550.

A. Chevinsky, "CEA in Tumors of Other Than Colorectal Origin", Seminars in Surgical Oncology, 1991, vol. 7, No. 3, pp. 162-166.

S. Schölzel, et al., "Carcinoembryonic Antigen Family Members CEACAM6 and CEACAM7 are Differentially Expressed in Normal Tissues and Oppositely Deregulated in Hyperplastic Colorectal Polyps and Early Adenomas", American Journal of Pathology, 2000, vol. 156, No. 2, pp. 595-605.

C. Ordoñez, et al., "Human Carcinoembryonic Antigen Functions as a General Inhibitor of Anoikis[1]", Cancer Research, Jul. 1, 2000, vol. 60, No. 13, pp. 3419-3424.

C.J. Sippel, et al., "Bile Acid Efflux Mediated by the Rat Liver Canalicular Bile Acid Transport/Ecto-Atpase Protein Requires Serine 503 Phosphorylation and Is Regulated by Tyrosine 488 Phosphyorylation", The Journal of Biological Chemistry, 1994, vol. 269, No. 39, pp. 19539-19545.

J. Brümmer, et al., "Association of pp60$^{C-SRC}$ with Biliary Glycoprotein (CD66a), An Adhesion Molecule of the Carcinoembryonic Antigen Family Downregulated in Colorectal Carcinomas", Oncogene, 1995, vol. 11, No. 8, pp. 1649-1655.

N. Beauchemin, et al., "Association of Biliary Glycoprotein with Protein Tyrosine Phosphatase SHP-1 in Malignant Colon Epithelial Cells", Oncogene, 1997, vol. 14, No. 7, pp. 783-790.

Y. Satow, et al., "Phosphocholine Binding Immunoglobulin Fab McPC603 an X-ray Diffraction Study at 2.7 Å", J. Mol. Biol., 1986, vol. 190, No. 4, pp. 593-604.

G. Johnson, et al., "Kabat Database and Its Applications: Future Directions", Nucleic Acids Research, 2001, vol. 29, No. 1, pp. 205-206.

D. Coomber, et al., "Generation of Anti-p53 Fab Fragments from Individuals with Colorectal Cancer Using Phage Display", J. Immunol., 1999, vol. 163, No. 4, pp. 2276-2283.

A. Glas, et al., "Analysis of Rearranged Immunoglobulin Heavy Chain Variable Region Genes Obtained from a Bone Marrow Transplant (BMT) Recipient", Clin. Exp. Immunol., 1997, vol. 107, No. 2, pp. 372-380.

S. Akashi, et al., "Structural Characterization of Mouse Monoclonal Antibody 13-1 Against a Porphyrin Derivative: Identification of a Disulfide Bond in CDR-H3 of Mab13-1", Biochemical and Biophysical Research Communications, 1997, vol. 240, No. 3. pp. 566-572.

K. Alfthan, "Surface Plasmon Resonance Biosensors as a Tool in Antibody Engineering", Biosensors & Bioelectronics, 1998, vol. 13, No. 6, pp. 653-663.

H. Issaq, et al., "Breakthroughs and Views, The SELDI-TOF MS Approach to Proteomics: Protein Profiling and Biomarker Identification", Biochemical and Biophysical Research Communications, 2002, vol. 292, No. 3, pp. 587-592.

C. Bruns, et al., , Clinical Cancer Research, May 2000, vol. 6, No. 5, pp. 1936-1948.

M. Kaufmann, et al., "Crystal Structure of the Anti-His Tag Antibody 3D5 Single-Chain Fragment Complexed to its Antigen", J. Mol. Biol., 2002, vol. 318, No. 1. Pp. 135-147.

S. Islam, et al., "HAD, A Data Bank of Heavy-Atom Binding Sites in Protein Crystals: A Resource for Use in Multiple Isomorphous Replacement and Anomalous Scattering", Acta Cryst., 1998, D54, pp. 1199-1206.

C. Lersch, et al., "Randomized Phase II Study of SCH 66336 and Gemcitabine in the Treatment of Metastatic Adenocarcinoma of the Pancreas", Proceedings of ASCO, vol. 20, 2001, Abstract 608.

J. Hallborn, et al., "Automated Screening Procedure for High-Throughput Generation of Antibody Fragments", Biotechniques, vol. 33, 2002, pp. S30-S37.

Mark S. Duxbury, et al., "CEACAM6 as a novel target for indirect type 1 immunotoxin-based therapy in pancreatic adenocarcinoma", Biochemical and Biophysical Research Communications, vol. 317, 2004, pp. 837-843.

Mark. S. Duxbury, et al., "CEACAM6 gene silencing impairs anoikis resistance and in vivo metastatic ability of pancreatic adenocarcinoma cells", Oncogene, vol. 23, 2004, pp. 465-473.

Pranay D. Khare, et al., "Tumor Growth Suppression by a Retroviral Vector Displaying scFv Antibody to CEA and Carrying the iNOS Gene", Anticancer Research, vol. 22, 2002, pp. 2443-2446.

Masahide Kuroki, et al., "Specific Targeting Strategies of Cancer Gene Therapy Using a Single-Chain Variable Fragment (scFv) with a High Affinity for CEA", Anticancer Research, vol. 20, 2000, pp. 4067-4071.

Motomu Kuroki, et al., "Identification and comparison of residues critical for cell-adhesion activities of two neutrophil CD66 antigens, CEACAM6 and CEACAM8", Journal of Leukocyte Biology, vol. 70, Oct. 2001, pp. 543-550.

J. Sambrook, et al., "Molecular Cloning" A Laboratory Manual, Second Edition, 1989, pp. 1.74-1.84.

Howard D. Edington, et al., "Radioimmunoimaging of metastatic medullary carcinoma of the thyroid gland using an indium-111-labeled monoclonal antibody to CEA", Surgery, vol. 104, No. 6, 1988, pp. 1004-1010.

Peter Jantscheff, et al., Expression of CEACAM 6 in Resectable Colorectal Cancer: A Factor of Independent Prognostic Significance, Journal of Clinical Oncology, vol. 21, No. 19, Oct. 1, 2003, pp. 3638-3646.

Robert M. Sharkey, et al., "Evaluation of a Complementarity-Determining Region-Grafted (Humanized) Anti-Carcinoembryonic Antigen Monoclonal Antibody in Preclinical and Clinical Studies", Cancer Research (Suppl), vol. 55, Dec. 1, 1995, pp. 5935-5945.

Jose W. Saldanha, et al., "A humanized anti-CEACAM6 monoclonal antibody targeting pancreatic adenocarcinoma demonstrates potent in vitro and in vivo activity", Proceedings of the American Association for Cancer Research Annual Meeting, vol. 45, XP-002478052, Mar. 2004, 2 pages.

John M. Burke, MD, et al., "Radioimmunotherapy for Acute Leukemia", Cancer Control, vol. 9, No. 2, XP-008003555, Mar. 2002, pp. 106-113.

L. Strickland, et al., "Characterization of CEACAM6 as a Potential Therapy Target for Pancreatic Adenocarcinoma", Journal of Pathology, vol. 201, No. Supplement, XP-002478054, Sep. 2003, p. 2A.

Japanese Office Action mailed on Nov. 16, 2010 in corresponding Japanese Application No. 2007-506205 (Translation Only).

Office Action issued Apr. 26, 2011 in Japan Application No. 2007-506205 (With English Translation).

* cited by examiner

FIG. 4

Variable Chain Structural Alignments

Variable Heavy

```
                    FR1                           CDR1          FR2                   CDR2
1mcp1_h     EVKLVESGGGLVQPGGSLRLSCATSGFTFSDFYMEWVRQPPGKRLEWIAASRNKGNKYTT
ceacamh     EVQVVETGGGLVRPGNSLKLSCLTSGFTFSNYRMHWLRQPPGKRLEWIAVITVKSDNYGA
1mcp1_h         EEEEE       EE       EEEEEEEEE           EEEEEE        EE   B       EE FR3                                     CDR3                    FR4
1mcp1_h     EYSASVKGRFIVSRDTSQSILYLQMNALRAEDTAIYYCARNYYGSTWYF--DVWGAGTTV
ceacamh     KYAESVRGRFTISRDDSKSSVYLQMNRLREEDTATYYCCR----TPWVYAMDCWGQGTSV
1mcp1_h       B  EEEEEE          EEEEEE                GGG EEEEEEEEE     EE_  EEE 1mcp1_h     TVSSESAR-
ceacamh     IVSSAKTTP
#1mcp1_h    EE    B
```

Variable Light

```
                    FR1                           CDR1          FR2                   CDR2
1mcp1_l     DIVMTQSPSSLSVSAGERVTMSCKSSQSLLNSGNQKNFLAWYQQKPGQPPKLLIYGASTR
ceacaml     NIVLTQSPASLAVSLGQRATISCRASKSVSASGYI--YMHWYQQKPGQPPKLLISLASNL
1mcp1_l    EEEE    EEEE        EEEEEEE          B    B   EEEEEE        EE EE   EE FR3                           CDR3                    FR4
1mcp1_l     ESGVPDRFTGSGSGTDFTLTISSVQAEDLAVYYCQNDHSYPLTFGAGTKLEIKRADAA
ceacaml     ESGVPARFSGSGSGTDFTLNIHPVEEEDVATYYCQHSRELPLTFGAGTKLELK----
#1mcp1_l       EEEEEE   EEEEEE              EEEEEEE         EEB   EEEE        B
```

FIG. 6
Variable Light Chain Humanization

Version 1
```
LchainV1  DIVLTQSPDSLAVSLGERATINCRASKSVSASGYIYMHWYQQKPGQPPKLLIYLASNLES  60
                            CDR1                              CDR2
ceacamL   NIVLTQSPASLAVSLGQRATISCRASKSVSASGYIYMHWYQQKPGQPPKLLISLASNLES  60
          :******* ******* *****.********************************* ********

LchainV1  GVPDRFSGSGSGTDFTLTISSLQAEDVAVYYCQHSRELPLTFGGGTKVEI  110
                         CDR3
ceacamL   GVPARFSGSGSGTDFTLNIHPVEEEDVATYYCQHSRELPLTFGAGTKLEL  110
          ***.************.::  **..*************** ****.**:*:
```

Version 2
```
LchainV2  DIVLTQSPDSLAVSLGERATINCRASKSVSASGYIYMHWYQQKPGQPPKLLISLASNLES  60
                            CDR1                              CDR2
ceacamL   NIVLTQSPASLAVSLGQRATISCRASKSVSASGYIYMHWYQQKPGQPPKLLISLASNLES  60
          :******* ******* *****.*************************************

LchainV2  GVPDRFSGSGSGTDFTLTISSLQAEDVAVYYCQHSRELPLTFGGGTKVEI  110
                         CDR3
ceacamL   GVPARFSGSGSGTDFTLNIHPVEEEDVATYYCQHSRELPLTFGAGTKLEL  110
          ***.************.::  **..*************** ****.**:*:
```

Version 3
```
L-chain   NIVLTQSPDSLAVSLGERATINCRASKSVSASGYIYMHWYQQKPGQPPKLLIYLASNLES  60
                            CDR1                              CDR2
ceacamL   NIVLTQSPASLAVSLGQRATISCRASKSVSASGYIYMHWYQQKPGQPPKLLISLASNLES  60
          ******** ******* *****.********************************* ********

L-chain   GVPDRFSGSGSGTDFTLTISSLQAEDVAVYYCQHSRELPLTFGGGTKVEI  110
                         CDR3
ceacamL   GVPARFSGSGSGTDFTLNIHPVEEEDVATYYCQHSRELPLTFGAGTKLEL  110
          ***.************.::  **..*************** ****.**:*:
```

FIG. 7
Variable Heavy Chain Humanization

```
H-chain     EVQLVETGGGLVRPGNSLKLSCLTSGFTFSNYRMHWLRQPPGKRLEWIAVITVKSDNYGA   60
H-chainV1   EVQLVESGGGLVQPGGSLRLSCAASGFTFSNYRMHWVRQAPGKGLEWVGVITVKSDNYGA   60

H-chain     KYAESVRGRFTISRDDDSKSSVYLQMNRLREEDTATYYCCRTPWVYAMDCWGQGTLVTVSS  110
H-chainV1   KYAESVRGRFTISRDDSKNSLYLQMNSLKTEDTAVYYCARTPWVYAMDCWGQGTLVTVSS  120

H-chain     EVQLVETGGGLVRPGNSLKLSCLTSGFTFSNYRMHWLRQPPGKRLEWIAVITVKSDNYGA   60
H-chainV2   EVQLVESGGGLVQPGGSLRLSCATSGFTFSNYRMHWVRQAPGKGLEWIGVITVKSDNYGA   60

H-chain     KYAESVRGRFTISRDDDSKSSVYLQMNRLREEDTATYYCCRTPWVYAMDCWGQGTLVTVSS  110
H-chainV2   KYAESVRGRFTISRDDSKNSLYLQMNSLKTEDTAVYYCARTPWVYAMDCWGQGTLVTVSS  120

H-chain     EVQLVETGGGLVRPGNSLKLSCLTSGFTFSNYRMHWLRQPPGKRLEWIAVITVKSDNYGA   60
H-chainV3   EVQLVESGGGLVQPGGSLRLSCATSGFTFSNYRMHWLRQAPGKGLEWIGVITVKSDNYGA   60

H-chain     KYAESVRGRFTISRDDDSKSSVYLQMNRLREEDTATYYCCRTPWVYAMDCWGQGTLVTVSS  110
H-chainV3   KYAESVRGRFTISRDDSKNSLYLQMNSLKTEDTAVYYCCRTPWVYAMDCWGQGTLVTVSS  120
```

FIG. 11A
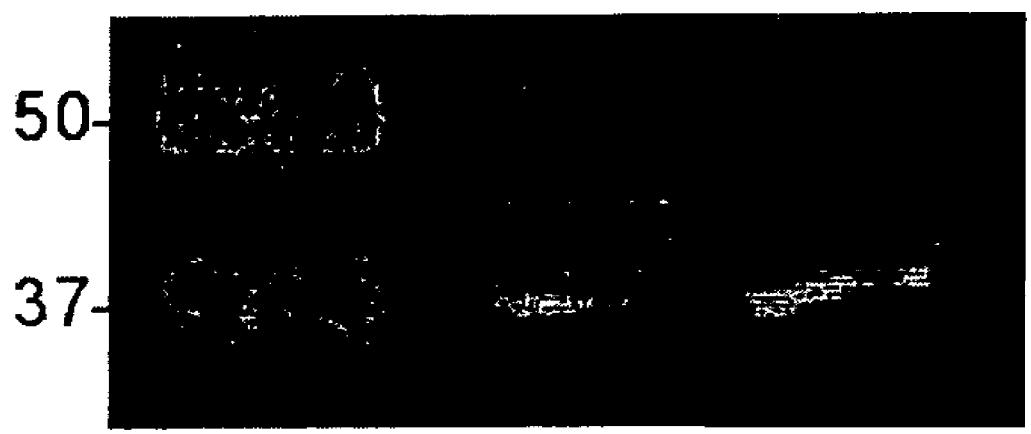
0 hr       6 hr
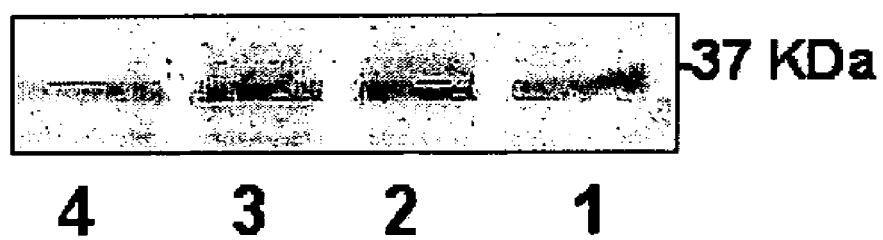
FIG. 11B

SEQUENCE LISTING

```
<160> NUMBER OF SEQ ID NOS: 36

<210> SEQ ID NO 1
<211> LENGTH: 218
<212> TYPE: PRT
<213> ORGANISM: Murine

<400> SEQUENCE: 1

Asn Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
            20                  25                  30

Gly Tyr Ile Tyr Met His Trp Tyr Gln Gln Lys Pro Gly Gln Pro Pro
        35                  40                  45

Lys Leu Leu Ile Ser Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Ser Arg
                85                  90                  95

Glu Leu Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 2
<211> LENGTH: 444
<212> TYPE: PRT
```

```
<213> ORGANISM: Murine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2
```

| | | | | | | | | | | | | | | | |
|---|---|---|---|---|---|---|---|---|---|---|---|---|---|---|---|
| Glu | Val | Gln | Xaa | Val | Glu | Thr | Gly | Gly | Gly | Leu | Val | Arg | Pro | Gly | Asn |
| 1 | | | 5 | | | | | | 10 | | | | | 15 | |
| Ser | Leu | Lys | Leu | Ser | Cys | Leu | Thr | Ser | Gly | Phe | Thr | Phe | Ser | Asn | Tyr |
| | | | 20 | | | | | 25 | | | | | 30 | | |
| Arg | Met | His | Trp | Leu | Arg | Gln | Pro | Pro | Gly | Lys | Arg | Leu | Glu | Trp | Ile |
| | | 35 | | | | | 40 | | | | | 45 | | | |
| Ala | Val | Ile | Thr | Val | Lys | Ser | Asp | Asn | Tyr | Gly | Ala | Lys | Tyr | Ala | Glu |
| 50 | | | | | 55 | | | | | 60 | | | | | |
| Ser | Val | Arg | Gly | Arg | Phe | Thr | Ile | Ser | Arg | Asp | Asp | Ser | Lys | Ser | Ser |
| 65 | | | | | 70 | | | | | 75 | | | | | 80 |
| Val | Tyr | Leu | Gln | Met | Asn | Arg | Leu | Arg | Glu | Glu | Asp | Thr | Ala | Thr | Tyr |
| | | | | 85 | | | | | 90 | | | | | 95 | |
| Tyr | Cys | Cys | Arg | Thr | Pro | Trp | Val | Tyr | Ala | Met | Asp | Cys | Trp | Gly | Gln |
| | | | 100 | | | | | 105 | | | | | 110 | | |
| Gly | Thr | Ser | Val | Ile | Val | Ser | Ser | Ala | Lys | Thr | Thr | Pro | Pro | Ser | Val |
| | | 115 | | | | | 120 | | | | | 125 | | | |
| Tyr | Pro | Leu | Ala | Pro | Gly | Ser | Ala | Ala | Gln | Thr | Asn | Ser | Met | Val | Thr |
| | | 130 | | | | | 135 | | | | | 140 | | | |
| Leu | Gly | Cys | Leu | Val | Lys | Gly | Tyr | Phe | Pro | Glu | Pro | Val | Thr | Val | Thr |
| 145 | | | | | 150 | | | | | 155 | | | | | 160 |
| Trp | Asn | Ser | Gly | Ser | Leu | Ser | Ser | Gly | Val | His | Thr | Phe | Pro | Ala | Val |
| | | | 165 | | | | | 170 | | | | | 175 | | |
| Leu | Gln | Ser | Asp | Leu | Tyr | Thr | Leu | Ser | Ser | Ser | Val | Thr | Val | Pro | Ser |
| | | | 180 | | | | | 185 | | | | | 190 | | |
| Ser | Thr | Trp | Pro | Ser | Glu | Thr | Val | Thr | Cys | Asn | Val | Ala | His | Pro | Ala |
| | | 195 | | | | | 200 | | | | | 205 | | | |
| Ser | Ser | Thr | Lys | Val | Asp | Lys | Lys | Ile | Val | Pro | Arg | Asp | Cys | Gly | Cys |
| 210 | | | | | 215 | | | | | 220 | | | | | |
| Lys | Pro | Cys | Ile | Cys | Thr | Val | Pro | Glu | Val | Ser | Ser | Val | Phe | Ile | Phe |
| 225 | | | | | 230 | | | | | 235 | | | | | 240 |
| Pro | Pro | Lys | Pro | Lys | Asp | Val | Leu | Thr | Ile | Thr | Leu | Thr | Pro | Lys | Val |
| | | | 245 | | | | | 250 | | | | | 255 | | |
| Thr | Cys | Val | Val | Val | Asp | Ile | Ser | Lys | Asp | Asp | Pro | Glu | Val | Gln | Phe |
| | | | 260 | | | | | 265 | | | | | 270 | | |
| Ser | Trp | Phe | Val | Asp | Asp | Val | Glu | Val | His | Thr | Ala | Gln | Thr | Gln | Pro |
| | | 275 | | | | | 280 | | | | | 285 | | | |
| Arg | Glu | Glu | Gln | Phe | Asn | Ser | Thr | Phe | Arg | Ser | Val | Ser | Glu | Leu | Pro |
| | | 290 | | | | | 295 | | | | | 300 | | | |
| Ile | Met | His | Gln | Asp | Trp | Leu | Asn | Gly | Lys | Glu | Phe | Lys | Cys | Arg | Val |
| 305 | | | | | 310 | | | | | 315 | | | | | 320 |
| Asn | Ser | Ala | Ala | Phe | Pro | Ala | Pro | Ile | Glu | Lys | Thr | Ile | Ser | Lys | Thr |
| | | | 325 | | | | | 330 | | | | | 335 | | |
| Lys | Gly | Arg | Pro | Lys | Ala | Pro | Gln | Val | Tyr | Thr | Ile | Pro | Pro | Pro | Lys |
| | | | 340 | | | | | 345 | | | | | 350 | | |
| Glu | Gln | Met | Ala | Lys | Asp | Lys | Val | Ser | Leu | Thr | Cys | Met | Ile | Thr | Asp |
| | | 355 | | | | | 360 | | | | | 365 | | | |
| Phe | Phe | Pro | Glu | Asp | Ile | Thr | Val | Glu | Trp | Gln | Trp | Asn | Gly | Gln | Pro |
| 370 | | | | | 375 | | | | | 380 | | | | | |

```
                Ala Glu Asn Tyr Lys Asn Thr Gln Pro Ile Met Asp Thr Asp Gly Ser
                385                 390                 395                 400

Tyr Phe Val Tyr Ser Lys Leu Asn Val Gln Lys Ser Asn Trp Glu Ala
                                405                 410                 415

Gly Asn Thr Phe Thr Cys Ser Val Leu His Glu Gly Leu His Asn His
                            420                 425                 430

His Thr Glu Lys Ser Leu Ser His Ser Pro Gly Lys
                        435                 440

<210> SEQ ID NO 3
<211> LENGTH: 740
<212> TYPE: DNA
<213> ORGANISM: Murine
<220> FEATURE:
<221> NAME/KEY: CDS
<222> LOCATION: (3)..(734)

<400> SEQUENCE: 3 cc atg gaa gtg cag ctg gtg gaa acc ggc ggc ggc ctg gtg cgt ccg         47
   Met Glu Val Gln Leu Val Glu Thr Gly Gly Gly Leu Val Arg Pro
   1               5                   10                  15 ggc aac agc ctg aaa ctg agc tgc ctg acc agc ggc ttt acc ttt agc        95
Gly Asn Ser Leu Lys Leu Ser Cys Leu Thr Ser Gly Phe Thr Phe Ser
                20                  25                  30 aac tat cgt atg cat tgg ctg cgt cag ccg ccg ggc aaa cgt ctg gaa       143
Asn Tyr Arg Met His Trp Leu Arg Gln Pro Pro Gly Lys Arg Leu Glu
            35                  40                  45 tgg att gcg gtg att acc gtg aaa agc gat aac tat ggc gcg aaa tat       191
Trp Ile Ala Val Ile Thr Val Lys Ser Asp Asn Tyr Gly Ala Lys Tyr
        50                  55                  60 gcg gaa agc gtg cgt ggc cgt ttt acc att agc cgt gat gat agc aaa       239
Ala Glu Ser Val Arg Gly Arg Phe Thr Ile Ser Arg Asp Asp Ser Lys
65                  70                  75 agc agc gtg tat ctg cag atg aac cgt ctg cgt gaa gaa gat acc gcg       287
Ser Ser Val Tyr Leu Gln Met Asn Arg Leu Arg Glu Glu Asp Thr Ala
 80                  85                  90                  95 acc tat tat tgc tgc cgt acc ccg tgg gtg tat gcg atg gat tgc tgg       335
Thr Tyr Tyr Cys Cys Arg Thr Pro Trp Val Tyr Ala Met Asp Cys Trp
                100                 105                 110 ggc ggc ggc ggc agc ggc ggc ggc agc tgc ggc ggc ggc agc                383
Gly Gly Gly Gly Ser Gly Gly Gly Ser Cys Gly Gly Gly Ser
            115                 120                 125 aac att gtg ctg acc cag agc ccg gcg agc ctg gcg gtg agc ctg ggc       431
Asn Ile Val Leu Thr Gln Ser Pro Ala Ser Leu Ala Val Ser Leu Gly
        130                 135                 140 cag cgt gcg acc att agc tgc cgt gcg agc aaa agc gtg agc gcg agc       479
Gln Arg Ala Thr Ile Ser Cys Arg Ala Ser Lys Ser Val Ser Ala Ser
    145                 150                 155 ggc tat att tat atg cat tgg tat cag cag aaa ccg ggc cag ccg ccg       527
Gly Tyr Ile Tyr Met His Trp Tyr Gln Gln Lys Pro Gly Gln Pro Pro
160                 165                 170                 175 aaa ctg ctg att agc ctg gcg agc aac ctg gaa agc ggc gtg ccg gcg       575
Lys Leu Leu Ile Ser Leu Ala Ser Asn Leu Glu Ser Gly Val Pro Ala
                180                 185                 190 cgt ttt agc ggc agc ggc agc ggc acc gat ttt acc ctg aac att cat       623
Arg Phe Ser Gly Ser Gly Ser Gly Thr Asp Phe Thr Leu Asn Ile His
            195                 200                 205 ccg gtg gaa gaa gaa gat gtg gcg acc tat tat tgc cag cat agc cgt       671
Pro Val Glu Glu Glu Asp Val Ala Thr Tyr Tyr Cys Gln His Ser Arg
        210                 215                 220 gaa ctg ccg ctg acc ttt ggc gcg ggc acc aaa ctg gaa ctg cat cat       719
```

```
Glu Leu Pro Leu Thr Phe Gly Ala Gly Thr Lys Leu Glu Leu His His
            225                 230                 235 cat cat cat cat taa ggatcc                                              740
His His His His
240

<210> SEQ ID NO 4
<211> LENGTH: 243
<212> TYPE: PRT
<213> ORGANISM: Murine

<400> SEQUENCE: 4

Met Glu Val Gln Leu Val Glu Thr Gly Gly Gly Leu Val Arg Pro Gly
  1               5                  10                  15

Asn Ser Leu Lys Leu Ser Cys Leu Thr Ser Gly Phe Thr Phe Ser Asn
             20                  25                  30

Tyr Arg Met His Trp Leu Arg Gln Pro Pro Gly Lys Arg Leu Glu Trp
         35                  40                  45

Ile Ala Val Ile Thr Val Lys Ser Asp Asn Tyr Gly Ala Lys Tyr Ala
     50                  55                  60

Glu Ser Val Arg Gly Arg Phe Thr Ile Ser Arg Asp Asp Ser Lys Ser
 65                  70                  75                  80

Ser Val Tyr Leu Gln Met Asn Arg Leu Arg Glu Glu Asp Thr Ala Thr
                 85                  90                  95

Tyr Tyr Cys Cys Arg Thr Pro Trp Val Tyr Ala Met Asp Cys Trp Gly
            100                 105                 110

Gly Gly Gly Ser Gly Gly Gly Gly Ser Cys Gly Gly Gly Gly Ser Asn
        115                 120                 125

Ile Val Leu Thr Gln Ser Pro Ala Ser Leu Ala Val Ser Leu Gly Gln
    130                 135                 140

Arg Ala Thr Ile Ser Cys Arg Ala Ser Lys Ser Val Ser Ala Ser Gly
145                 150                 155                 160

Tyr Ile Tyr Met His Trp Tyr Gln Gln Lys Pro Gly Gln Pro Pro Lys
                165                 170                 175

Leu Leu Ile Ser Leu Ala Ser Asn Leu Glu Ser Gly Val Pro Ala Arg
            180                 185                 190

Phe Ser Gly Ser Gly Ser Gly Thr Asp Phe Thr Leu Asn Ile His Pro
        195                 200                 205

Val Glu Glu Glu Asp Val Ala Thr Tyr Tyr Cys Gln His Ser Arg Glu
    210                 215                 220

Leu Pro Leu Thr Phe Gly Ala Gly Thr Lys Leu Glu Leu His His His
225                 230                 235                 240

His His His

<210> SEQ ID NO 5
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 5 cc atg gaa gtg cag ctg gtg gaa agc ggc ggc ggc ctg gtg cag ccg     47
   Met Glu Val Gln Leu Val Glu Ser Gly Gly Gly Leu Val Gln Pro
     1               5                  10                  15 ggc ggc agc ctg cgt ctg agc tgc gcg gcg agc ggc ttt acc ttt agc     95
```

```
Gly Gly Ser Leu Arg Leu Ser Cys Ala Ala Ser Gly Phe Thr Phe Ser
            20                  25                  30 aac tat cgt atg cat tgg gtg cgt cag gcg ccg ggc aaa ggc ctg gaa      143
Asn Tyr Arg Met His Trp Val Arg Gln Ala Pro Gly Lys Gly Leu Glu
                35                  40                  45 tgg gtg ggc gtg att acc gtg aaa agc gat aac tat ggc gcg aaa tat      191
Trp Val Gly Val Ile Thr Val Lys Ser Asp Asn Tyr Gly Ala Lys Tyr
        50                  55                  60 gcg gaa agc gtg cgt ggc cgt ttt acc att agc cgt gat gat agc aaa      239
Ala Glu Ser Val Arg Gly Arg Phe Thr Ile Ser Arg Asp Asp Ser Lys
65                  70                  75                  80 aac agc ctg tat ctg cag atg aac agc ctg aaa acc gaa gat acc gcg      287
Asn Ser Leu Tyr Leu Gln Met Asn Ser Leu Lys Thr Glu Asp Thr Ala
                85                  90                  95 gtg tat tat tgc gcg cgt acc ccg tgg gtg tat gcg atg gat tgc tgg      335
Val Tyr Tyr Cys Ala Arg Thr Pro Trp Val Tyr Ala Met Asp Cys Trp
            100                 105                 110 ggc cag ggc acc ctg gtg acc gtg agc agc ggc ggc gga agc ggc          383
Gly Gln Gly Thr Leu Val Thr Val Ser Ser Gly Gly Gly Ser Gly
                115                 120                 125 ggt ggc ggc agc tgc ggc ggc ggc agc gac att gtg ctg acc cag          431
Gly Gly Gly Ser Cys Gly Gly Gly Ser Asp Ile Val Leu Thr Gln
        130                 135                 140 agc ccg gat agc ctg gcg gtg agc ctg ggc gaa cgt gcg acc att aac      479
Ser Pro Asp Ser Leu Ala Val Ser Leu Gly Glu Arg Ala Thr Ile Asn
    145                 150                 155 tgc cgt gcg agc aaa agc gtg agc gcg agc ggc tat att tat atg cat      527
Cys Arg Ala Ser Lys Ser Val Ser Ala Ser Gly Tyr Ile Tyr Met His
160                 165                 170                 175 tgg tat cag cag aaa ccg ggc cag ccg ccg aaa ctg ctg att tat ctg      575
Trp Tyr Gln Gln Lys Pro Gly Gln Pro Pro Lys Leu Leu Ile Tyr Leu
                180                 185                 190 gcg agc aac ctg gaa agc ggc gtg ccg gat cgt ttt agc ggc agc ggc      623
Ala Ser Asn Leu Glu Ser Gly Val Pro Asp Arg Phe Ser Gly Ser Gly
            195                 200                 205 agc ggc acc gat ttt acc ctg acc att agc agc ctg cag gcg gaa gat      671
Ser Gly Thr Asp Phe Thr Leu Thr Ile Ser Ser Leu Gln Ala Glu Asp
        210                 215                 220 gtg gcg gtg tat tat tgc cag cat agc cgt gaa ctg ccg ctg acc ttt      719
Val Ala Val Tyr Tyr Cys Gln His Ser Arg Glu Leu Pro Leu Thr Phe
225                 230                 235 ggc ggc ggc acc aaa gtg gaa att aaa cat cat cat cat cat taa          767
Gly Gly Gly Thr Lys Val Glu Ile Lys His His His His His His
                245                 250 ggatcc                                                                773

<210> SEQ ID NO 6
<211> LENGTH: 254
<212> TYPE: PRT
<213> ORGANISM: Artificial Sequence
<220> FEATURE:
<223> OTHER INFORMATION: Synthetic Construct

<400> SEQUENCE: 6

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Asn
            20                  25                  30

Tyr Arg Met His Trp Val Arg Gln Ala Pro Gly Lys Gly Leu Glu Trp
        35                  40                  45
```

```
Val Gly Val Ile Thr Val Lys Ser Asp Asn Tyr Gly Ala Lys Tyr Ala
     50                  55                  60

Glu Ser Val Arg Gly Arg Phe Thr Ile Ser Arg Asp Asp Ser Lys Asn
 65                  70                  75                  80

Ser Leu Tyr Leu Gln Met Asn Ser Leu Lys Thr Glu Asp Thr Ala Val
                 85                  90                  95

Tyr Tyr Cys Ala Arg Thr Pro Trp Val Tyr Ala Met Asp Cys Trp Gly
            100                 105                 110

Gln Gly Thr Leu Val Thr Val Ser Gly Gly Gly Ser Gly Gly
        115                 120                 125

Gly Gly Ser Cys Gly Gly Gly Ser Asp Ile Val Leu Thr Gln Ser
        130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
                165                 170                 175

Tyr Gln Gln Lys Pro Gly Gln Pro Pro Lys Leu Leu Ile Tyr Leu Ala
                180                 185                 190

Ser Asn Leu Glu Ser Gly Val Pro Asp Arg Phe Ser Gly Ser Gly Ser
                195                 200                 205

Gly Thr Asp Phe Thr Leu Thr Ile Ser Ser Leu Gln Ala Glu Asp Val
        210                 215                 220

Ala Val Tyr Tyr Cys Gln His Ser Arg Glu Leu Pro Leu Thr Phe Gly
225                 230                 235                 240

Gly Gly Thr Lys Val Glu Ile Lys His His His His His His
                245                 250

<210> SEQ ID NO 7
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 7 cc atg gaa gtg cag ctg gtg gaa agc ggc ggc ggc ctg gtg cag ccg      47
   Met Glu Val Gln Leu Val Glu Ser Gly Gly Gly Leu Val Gln Pro
    1               5                  10                  15 ggc ggc agc ctg cgt ctg agc tgc gcg acc agc ggc ttt acc ttt agc     95
Gly Gly Ser Leu Arg Leu Ser Cys Ala Thr Ser Gly Phe Thr Phe Ser
             20                  25                  30 aac tat cgt atg cat tgg gtg cgt cag gcg ccg ggc aaa ggc ctg gaa    143
Asn Tyr Arg Met His Trp Val Arg Gln Ala Pro Gly Lys Gly Leu Glu
         35                  40                  45 tgg att ggc gtg att acc gtg aaa agc gat aac tat ggc gcg aaa tat    191
Trp Ile Gly Val Ile Thr Val Lys Ser Asp Asn Tyr Gly Ala Lys Tyr
     50                  55                  60 gcg gaa agc gtg cgt ggc cgt ttt acc att agc cgt gat gat agc aaa    239
Ala Glu Ser Val Arg Gly Arg Phe Thr Ile Ser Arg Asp Asp Ser Lys
 65                  70                  75 aac agc ctg tat ctg cag atg aac agc ctg aaa acc gaa gat acc gcg    287
Asn Ser Leu Tyr Leu Gln Met Asn Ser Leu Lys Thr Glu Asp Thr Ala
 80                  85                  90                  95 gtg tat tat tgc gcg cgt acc ccg tgg gtg tat gcg atg gat tgc tgg    335
Val Tyr Tyr Cys Ala Arg Thr Pro Trp Val Tyr Ala Met Asp Cys Trp
                100                 105                 110
```

| | | |
|---|---|---|
| ggc cag ggc acc ctg gtg acc gtg agc agc ggc ggc ggc gga agc ggc<br>Gly Gln Gly Thr Leu Val Thr Val Ser Ser Gly Gly Gly Gly Ser Gly<br>115                      120                  125 | 383 |
| ggt ggc ggc agc tgc ggc ggc ggc agc gac att gtg ctg acc cag<br>Gly Gly Gly Ser Cys Gly Gly Gly Ser Asp Ile Val Leu Thr Gln<br>130                  135                  140 | 431 |
| agc ccg gat agc ctg gcg gtg agc ctg ggc gaa cgt gcg acc att aac<br>Ser Pro Asp Ser Leu Ala Val Ser Leu Gly Glu Arg Ala Thr Ile Asn<br>145                      150                  155 | 479 |
| tgc cgt gcg agc aaa agc gtg agc gcg agc ggc tat att tat atg cat<br>Cys Arg Ala Ser Lys Ser Val Ser Ala Ser Gly Tyr Ile Tyr Met His<br>160                 165                 170                175 | 527 |
| tgg tat cag cag aaa ccg ggc cag ccg ccg aaa ctg ctg att tat ctg<br>Trp Tyr Gln Gln Lys Pro Gly Gln Pro Pro Lys Leu Leu Ile Tyr Leu<br>                    180                  185                  190 | 575 |
| gcg agc aac ctg gaa agc ggc gtg ccg gat cgt ttt agc ggc agc ggc<br>Ala Ser Asn Leu Glu Ser Gly Val Pro Asp Arg Phe Ser Gly Ser Gly<br>                  195                  200                  205 | 623 |
| agc ggc acc gat ttt acc ctg acc att agc agc ctg cag gcg gaa gat<br>Ser Gly Thr Asp Phe Thr Leu Thr Ile Ser Ser Leu Gln Ala Glu Asp<br>210                      215                  220 | 671 |
| gtg gcg gtg tat tat tgc cag cat agc cgt gaa ctg ccg ctg acc ttt<br>Val Ala Val Tyr Tyr Cys Gln His Ser Arg Glu Leu Pro Leu Thr Phe<br>225                      230                  235 | 719 |
| ggc ggc ggc acc aaa gtg gaa att aaa cat cat cat cat cat cat taa<br>Gly Gly Gly Thr Lys Val Glu Ile Lys His His His His His His<br>240                      245                  250 | 767 |
| ggatcc | 773 |

<210> SEQ ID NO 8
<211> LENGTH: 254
<212> TYPE: PRT
<213> ORGANISM: Artificial Sequence
<220> FEATURE:
<223> OTHER INFORMATION: Synthetic Construct

<400> SEQUENCE: 8

Met Glu Val Gln Leu Val Glu Ser Gly Gly Gly Leu Val Gln Pro Gly
1               5                   10                  15

Gly Ser Leu Arg Leu Ser Cys Ala Thr Ser Gly Phe Thr Phe Ser Asn
            20                  25                  30

Tyr Arg Met His Trp Val Arg Gln Ala Pro Gly Lys Gly Leu Glu Trp
        35                  40                  45

Ile Gly Val Ile Thr Val Lys Ser Asp Asn Tyr Gly Ala Lys Tyr Ala
    50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
                85                  90                  95

Tyr Tyr Cys Ala Arg Thr Pro Trp Val Tyr Ala Met Asp Cys Trp Gly
            100                 105                 110

Gln Gly Thr Leu Val Thr Val Ser Ser Gly Gly Gly Gly Ser Gly Gly
        115                 120                 125

Gly Gly Ser Cys Gly Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
                165                 170                 175

```
Tyr Gln Lys Pro Gly Gln Pro Lys Leu Leu Ile Tyr Leu Ala
            180                 185                 190

Ser Asn Leu Glu Ser Gly Val Pro Asp Arg Phe Ser Gly Ser Gly Ser
            195                 200                 205

Gly Thr Asp Phe Thr Leu Thr Ile Ser Ser Leu Gln Ala Glu Asp Val
210                 215                 220

Ala Val Tyr Tyr Cys Gln His Ser Arg Glu Leu Pro Leu Thr Phe Gly
225                 230                 235                 240

Gly Gly Thr Lys Val Glu Ile Lys His His His His His His
            245                 250

<210> SEQ ID NO 9
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 9
```

| | | | | | | | | | | | | | | | | |
|---|---|---|---|---|---|---|---|---|---|---|---|---|---|---|---|---|
| cc | atg | gaa | gtg | cag | ctg | gtg | gaa | agc | ggc | ggc | ggc | ctg | gtg | cag | ccg | 47 |
| | Met | Glu | Val | Gln | Leu | Val | Glu | Ser | Gly | Gly | Gly | Leu | Val | Gln | Pro | |
| | 1 | | | 5 | | | | | 10 | | | | | 15 | | |
| ggc | ggc | agc | ctg | cgt | ctg | agc | tgc | gcg | acc | agc | ggc | ttt | acc | ttt | agc | 95 |
| Gly | Gly | Ser | Leu | Arg | Leu | Ser | Cys | Ala | Thr | Ser | Gly | Phe | Thr | Phe | Ser | |
| | | | 20 | | | | | 25 | | | | | 30 | | | |
| aac | tat | cgt | atg | cat | tgg | ctg | cgt | cag | gcg | ccg | ggc | aaa | ggc | ctg | gaa | 143 |
| Asn | Tyr | Arg | Met | His | Trp | Leu | Arg | Gln | Ala | Pro | Gly | Lys | Gly | Leu | Glu | |
| | | 35 | | | | | 40 | | | | | 45 | | | | |
| tgg | att | ggc | gtg | att | acc | gtg | aaa | agc | gat | aac | tat | ggc | gcg | aaa | tat | 191 |
| Trp | Ile | Gly | Val | Ile | Thr | Val | Lys | Ser | Asp | Asn | Tyr | Gly | Ala | Lys | Tyr | |
| | | 50 | | | | | 55 | | | | | 60 | | | | |
| gcg | gaa | agc | gtg | cgt | ggc | cgt | ttt | acc | att | agc | cgt | gat | gat | agc | aaa | 239 |
| Ala | Glu | Ser | Val | Arg | Gly | Arg | Phe | Thr | Ile | Ser | Arg | Asp | Asp | Ser | Lys | |
| 65 | | | | | 70 | | | | | 75 | | | | | | |
| aac | agc | ctg | tat | ctg | cag | atg | aac | agc | ctg | aaa | acc | gaa | gat | acc | gcg | 287 |
| Asn | Ser | Leu | Tyr | Leu | Gln | Met | Asn | Ser | Leu | Lys | Thr | Glu | Asp | Thr | Ala | |
| 80 | | | | | 85 | | | | | 90 | | | | | 95 | |
| gtg | tat | tat | tgc | tgc | cgt | acc | ccg | tgg | gtg | tat | gcg | atg | gat | tgc | tgg | 335 |
| Val | Tyr | Tyr | Cys | Cys | Arg | Thr | Pro | Trp | Val | Tyr | Ala | Met | Asp | Cys | Trp | |
| | | | 100 | | | | | 105 | | | | | 110 | | | |
| ggc | cag | ggc | acc | ctg | gtg | acc | gtg | agc | agc | ggc | ggc | gga | agc | ggc | | 383 |
| Gly | Gln | Gly | Thr | Leu | Val | Thr | Val | Ser | Ser | Gly | Gly | Gly | Ser | Gly | | |
| | | | 115 | | | | | 120 | | | | | 125 | | | |
| ggt | ggc | ggc | agc | tgc | ggc | ggc | ggc | agc | gac | att | gtg | ctg | acc | cag | | 431 |
| Gly | Gly | Gly | Ser | Cys | Gly | Gly | Gly | Ser | Asp | Ile | Val | Leu | Thr | Gln | | |
| | | 130 | | | | | 135 | | | | | 140 | | | | |
| agc | ccg | gat | agc | ctg | gcg | gtg | agc | ctg | ggc | gaa | cgt | gcg | acc | att | aac | 479 |
| Ser | Pro | Asp | Ser | Leu | Ala | Val | Ser | Leu | Gly | Glu | Arg | Ala | Thr | Ile | Asn | |
| | 145 | | | | | 150 | | | | | 155 | | | | | |
| tgc | cgt | gcg | agc | aaa | agc | gtg | agc | gcg | agc | ggc | tat | att | tat | atg | cat | 527 |
| Cys | Arg | Ala | Ser | Lys | Ser | Val | Ser | Ala | Ser | Gly | Tyr | Ile | Tyr | Met | His | |
| 160 | | | | | 165 | | | | | 170 | | | | | 175 | |
| tgg | tat | cag | cag | aaa | ccg | ggc | cag | ccg | ccg | aaa | ctg | ctg | att | tat | ctg | 575 |
| Trp | Tyr | Gln | Gln | Lys | Pro | Gly | Gln | Pro | Pro | Lys | Leu | Leu | Ile | Tyr | Leu | |
| | | | 180 | | | | | 185 | | | | | 190 | | | |
| gcg | agc | aac | ctg | gaa | agc | ggc | gtg | ccg | gat | cgt | ttt | agc | ggc | agc | ggc | 623 |
| Ala | Ser | Asn | Leu | Glu | Ser | Gly | Val | Pro | Asp | Arg | Phe | Ser | Gly | Ser | Gly | |
| | | 195 | | | | | 200 | | | | | 205 | | | | |

```
agc ggc acc gat ttt acc ctg acc att agc agc ctg cag gcg gaa gat    671
Ser Gly Thr Asp Phe Thr Leu Thr Ile Ser Ser Leu Gln Ala Glu Asp
        210                 215                 220 gtg gcg gtg tat tat tgc cag cat agc cgt gaa ctg ccg ctg acc ttt    719
Val Ala Val Tyr Tyr Cys Gln His Ser Arg Glu Leu Pro Leu Thr Phe
225                 230                 235 ggc ggc ggc acc aaa gtg gaa att aaa cat cat cat cat cat taa        767
Gly Gly Gly Thr Lys Val Glu Ile Lys His His His His His
240                 245                 250 ggatcc                                                             773

<210> SEQ ID NO 10
<211> LENGTH: 254
<212> TYPE: PRT
<213> ORGANISM: Artificial Sequence
<220> FEATURE:
<223> OTHER INFORMATION: Synthetic Construct

<400> SEQUENCE: 10

Met Glu Val Gln Leu Val Glu Ser Gly Gly Gly Leu Val Gln Pro Gly
1               5                   10                  15

Gly Ser Leu Arg Leu Ser Cys Ala Thr Ser Gly Phe Thr Phe Ser Asn
            20                  25                  30

Tyr Arg Met His Trp Leu Arg Gln Ala Pro Gly Lys Gly Leu Glu Trp
        35                  40                  45

Ile Gly Val Ile Thr Val Lys Ser Asp Asn Tyr Gly Ala Lys Tyr Ala
    50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
                85                  90                  95

Tyr Tyr Cys Cys Arg Thr Pro Trp Val Tyr Ala Met Asp Cys Trp Gly
            100                 105                 110

Gln Gly Thr Leu Val Thr Val Ser Gly Gly Gly Ser Gly Gly
        115                 120                 125

Gly Gly Ser Cys Gly Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
                165                 170                 175

Tyr Gln Gln Lys Pro Gly Gln Pro Pro Lys Leu Leu Ile Tyr Leu Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln His Ser Arg Glu Leu Pro Leu Thr Phe Gly
225                 230                 235                 240

Gly Gly Thr Lys Val Glu Ile Lys His His His His His
                245                 250

<210> SEQ ID NO 11
<211> LENGTH: 773
<212> TYPE: DNA
<213> ORGANISM: Artificial Sequence
<220> FEATURE:
<223> OTHER INFORMATION: Synthetic Peptide
```

```
<220> FEATURE:
<221> NAME/KEY: CDS
<222> LOCATION: (3)..(767)

<400> SEQUENCE: 11 cc atg gaa gtg cag ctg gtg gaa agc ggc ggc ggc ctg gtg cag ccg      47
   Met Glu Val Gln Leu Val Glu Ser Gly Gly Gly Leu Val Gln Pro
   1               5                  10                  15 ggc ggc agc ctg cgt ctg agc tgc gcg gcg agc ggc ttt acc ttt agc     95
Gly Gly Ser Leu Arg Leu Ser Cys Ala Ala Ser Gly Phe Thr Phe Ser
             20                  25                  30 aac tat cgt atg cat tgg gtg cgt cag gcg ccg ggc aaa ggc ctg gaa    143
Asn Tyr Arg Met His Trp Val Arg Gln Ala Pro Gly Lys Gly Leu Glu
         35                  40                  45 tgg gtg ggc gtg att acc gtg aaa agc gat aac tat ggc gcg aaa tat    191
Trp Val Gly Val Ile Thr Val Lys Ser Asp Asn Tyr Gly Ala Lys Tyr
     50                  55                  60 gcg gaa agc gtg cgt ggc cgt ttt acc att agc cgt gat gat agc aaa    239
Ala Glu Ser Val Arg Gly Arg Phe Thr Ile Ser Arg Asp Asp Ser Lys
 65                  70                  75 aac agc ctg tat ctg cag atg aac agc ctg aaa acc gaa gat acc gcg    287
Asn Ser Leu Tyr Leu Gln Met Asn Ser Leu Lys Thr Glu Asp Thr Ala
 80                  85                  90                  95 gtg tat tat tgc gcg cgt acc ccg tgg gtg tat gcg atg gat tgc tgg    335
Val Tyr Tyr Cys Ala Arg Thr Pro Trp Val Tyr Ala Met Asp Cys Trp
                100                 105                 110 ggc cag ggc acc ctg gtg acc gtg agc agc ggc ggc gga agc ggc        383
Gly Gln Gly Thr Leu Val Thr Val Ser Ser Gly Gly Gly Ser Gly
             115                 120                 125 ggt ggc ggc agc tgc ggc ggc ggc agc gac att gtg ctg acc cag        431
Gly Gly Gly Ser Cys Gly Gly Gly Ser Asp Ile Val Leu Thr Gln
         130                 135                 140 agc ccg gat agc ctg gcg gtg agc ctg ggc gaa cgt gcg acc att aac    479
Ser Pro Asp Ser Leu Ala Val Ser Leu Gly Glu Arg Ala Thr Ile Asn
     145                 150                 155 tgc cgt gcg agc aaa agc gtg agc gcg agc ggc tat att tat atg cat    527
Cys Arg Ala Ser Lys Ser Val Ser Ala Ser Gly Tyr Ile Tyr Met His
160                 165                 170                 175 tgg tat cag cag aaa ccg ggc cag ccg ccg aaa ctg ctg att agc ctg    575
Trp Tyr Gln Gln Lys Pro Gly Gln Pro Pro Lys Leu Leu Ile Ser Leu
                180                 185                 190 gcg agc aac ctg gaa agc ggc gtg ccg gat cgt ttt agc ggc agc ggc    623
Ala Ser Asn Leu Glu Ser Gly Val Pro Asp Arg Phe Ser Gly Ser Gly
             195                 200                 205 agc ggc acc gat ttt acc ctg acc att agc agc ctg cag gcg gaa gat    671
Ser Gly Thr Asp Phe Thr Leu Thr Ile Ser Ser Leu Gln Ala Glu Asp
         210                 215                 220 gtg gcg gtg tat tat tgc cag cat agc cgt gaa ctg ccg ctg acc ttt    719
Val Ala Val Tyr Tyr Cys Gln His Ser Arg Glu Leu Pro Leu Thr Phe
 225                 230                 235 ggc ggc ggc acc aaa gtg gaa att aaa cat cat cat cat cat cat taa    767
Gly Gly Gly Thr Lys Val Glu Ile Lys His His His His His His
                240                 245                 250 ggatcc                                                              773

<210> SEQ ID NO 12
<211> LENGTH: 254
<212> TYPE: PRT
<213> ORGANISM: Artificial Sequence
<220> FEATURE:
<223> OTHER INFORMATION: Synthetic Construct
```

<400> SEQUENCE: 12

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Asn
            20                  25                  30

Tyr Arg Met His Trp Val Arg Gln Ala Pro Gly Lys Gly Leu Glu Trp
        35                  40                  45

Val Gly Val Ile Thr Val Lys Ser Asp Asn Tyr Gly Ala Lys Tyr Ala
    50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
                85                  90                  95

Tyr Tyr Cys Ala Arg Thr Pro Trp Val Tyr Ala Met Asp Cys Trp Gly
            100                 105                 110

Gln Gly Thr Leu Val Thr Val Ser Ser Gly Gly Gly Ser Gly Gly
        115                 120                 125

Gly Gly Ser Cys Gly Gly Gly Ser Asp Ile Val Leu Thr Gln Ser
130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
                165                 170                 175

Tyr Gln Gln Lys Pro Gly Gln Pro Pro Lys Leu Leu Ile Ser Leu Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln His Ser Arg Glu Leu Pro Leu Thr Phe Gly
225                 230                 235                 240

Gly Gly Thr Lys Val Glu Ile Lys His His His His His His
                245                 250
```

<210> SEQ ID NO 13
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 13

```
cc atg gaa gtg cag ctg gtg gaa agc ggc ggc ggc ctg gtg cag ccg      47
   Met Glu Val Gln Leu Val Glu Ser Gly Gly Gly Leu Val Gln Pro
   1               5                   10                  15 ggc ggc agc ctg cgt ctg agc tgc gcg acc agc ggc ttt acc ttt agc     95
Gly Gly Ser Leu Arg Leu Ser Cys Ala Thr Ser Gly Phe Thr Phe Ser
            20                  25                  30 aac tat cgt atg cat tgg gtg cgt cag gcg ccg ggc aaa ggc ctg gaa    143
Asn Tyr Arg Met His Trp Val Arg Gln Ala Pro Gly Lys Gly Leu Glu
        35                  40                  45 tgg att ggc gtg att acc gtg aaa agc gat aac tat ggc gcg aaa tat    191
Trp Ile Gly Val Ile Thr Val Lys Ser Asp Asn Tyr Gly Ala Lys Tyr
    50                  55                  60 gcg gaa agc gtg cgt ggc cgt ttt acc att agc cgt gat gat agc aaa    239
```

```
               Ala Glu Ser Val Arg Gly Arg Phe Thr Ile Ser Arg Asp Asp Ser Lys
                   65                  70                  75 aac agc ctg tat ctg cag atg aac agc ctg aaa acc gaa gat acc gcg         287
Asn Ser Leu Tyr Leu Gln Met Asn Ser Leu Lys Thr Glu Asp Thr Ala
 80                  85                  90                  95 gtg tat tat tgc gcg cgt acc ccg tgg gtg tat gcg atg gat tgc tgg         335
Val Tyr Tyr Cys Ala Arg Thr Pro Trp Val Tyr Ala Met Asp Cys Trp
                100                 105                 110 ggc cag ggc acc ctg gtg acc gtg agc agc ggc ggc gga agc ggc             383
Gly Gln Gly Thr Leu Val Thr Val Ser Ser Gly Gly Gly Ser Gly
                115                 120                 125 ggt ggc ggc agc tgc ggc ggc ggc agc gac att gtg ctg acc cag             431
Gly Gly Gly Ser Cys Gly Gly Gly Ser Asp Ile Val Leu Thr Gln
                130                 135                 140 agc ccg gat agc ctg gcg gtg agc ctg ggc gaa cgt gcg acc att aac         479
Ser Pro Asp Ser Leu Ala Val Ser Leu Gly Glu Arg Ala Thr Ile Asn
    145                 150                 155 tgc cgt gcg agc aaa agc gtg agc gcg agc ggc tat att tat atg cat         527
Cys Arg Ala Ser Lys Ser Val Ser Ala Ser Gly Tyr Ile Tyr Met His
160                 165                 170                 175 tgg tat cag cag aaa ccg ggc cag ccg ccg aaa ctg ctg att agc ctg         575
Trp Tyr Gln Gln Lys Pro Gly Gln Pro Pro Lys Leu Leu Ile Ser Leu
                180                 185                 190 gcg agc aac ctg gaa agc ggc gtg ccg gat cgt ttt agc ggc agc ggc         623
Ala Ser Asn Leu Glu Ser Gly Val Pro Asp Arg Phe Ser Gly Ser Gly
                195                 200                 205 agc ggc acc gat ttt acc ctg acc att agc agc ctg cag gcg gaa gat         671
Ser Gly Thr Asp Phe Thr Leu Thr Ile Ser Ser Leu Gln Ala Glu Asp
                210                 215                 220 gtg gcg gtg tat tat tgc cag cat agc cgt gaa ctg ccg ctg acc ttt         719
Val Ala Val Tyr Tyr Cys Gln His Ser Arg Glu Leu Pro Leu Thr Phe
225                 230                 235 ggc ggc ggc acc aaa gtg gaa att aaa cat cat cat cat cat cat taa         767
Gly Gly Gly Thr Lys Val Glu Ile Lys His His His His His His
                240                 245                 250 ggatcc                                                                  773
```

<210> SEQ ID NO 14
<211> LENGTH: 254
<212> TYPE: PRT
<213> ORGANISM: Artificial Sequence
<220> FEATURE:
<223> OTHER INFORMATION: Synthetic Construct

<400> SEQUENCE: 14

```
Met Glu Val Gln Leu Val Glu Ser Gly Gly Gly Leu Val Gln Pro Gly
 1               5                  10                  15

Gly Ser Leu Arg Leu Ser Cys Ala Thr Ser Gly Phe Thr Phe Ser Asn
                20                  25                  30

Tyr Arg Met His Trp Val Arg Gln Ala Pro Gly Lys Gly Leu Glu Trp
            35                  40                  45

Ile Gly Val Ile Thr Val Lys Ser Asp Asn Tyr Gly Ala Lys Tyr Ala
        50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
                85                  90                  95

Tyr Tyr Cys Ala Arg Thr Pro Trp Val Tyr Ala Met Asp Cys Trp Gly
            100                 105                 110
```

```
Gln Gly Thr Leu Val Thr Val Ser Ser Gly Gly Gly Ser Gly Gly
            115                 120                 125
Gly Gly Ser Cys Gly Gly Gly Ser Asp Ile Val Leu Thr Gln Ser
        130                 135                 140
Pro Asp Ser Leu Ala Val Ser Leu Gly Glu Arg Ala Thr Ile Asn Cys
145                 150                 155                 160
Arg Ala Ser Lys Ser Val Ser Ala Ser Gly Tyr Ile Tyr Met His Trp
                165                 170                 175
Tyr Gln Gln Lys Pro Gly Gln Pro Pro Lys Leu Leu Ile Ser Leu Ala
                180                 185                 190
Ser Asn Leu Glu Ser Gly Val Pro Asp Arg Phe Ser Gly Ser Gly Ser
                195                 200                 205
Gly Thr Asp Phe Thr Leu Thr Ile Ser Ser Leu Gln Ala Glu Asp Val
        210                 215                 220
Ala Val Tyr Tyr Cys Gln His Ser Arg Glu Leu Pro Leu Thr Phe Gly
225                 230                 235                 240
Gly Gly Thr Lys Val Glu Ile Lys His His His His His His
                245                 250

<210> SEQ ID NO 15
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 15 cc atg gaa gtg cag ctg gtg gaa agc ggc ggc ggc ctg gtg cag ccg        47
   Met Glu Val Gln Leu Val Glu Ser Gly Gly Gly Leu Val Gln Pro
   1               5                   10                  15 ggc ggc agc ctg cgt ctg agc tgc gcg acc agc ggc ttt acc ttt agc       95
Gly Gly Ser Leu Arg Leu Ser Cys Ala Thr Ser Gly Phe Thr Phe Ser
             20                  25                  30 aac tat cgt atg cat tgg ctg cgt cag gcg ccg ggc aaa ggc ctg gaa      143
Asn Tyr Arg Met His Trp Leu Arg Gln Ala Pro Gly Lys Gly Leu Glu
         35                  40                  45 tgg att ggc gtg att acc gtg aaa agc gat aac tat ggc gcg aaa tat      191
Trp Ile Gly Val Ile Thr Val Lys Ser Asp Asn Tyr Gly Ala Lys Tyr
     50                  55                  60 gcg gaa agc gtg cgt ggc cgt ttt acc att agc cgt gat gat agc aaa      239
Ala Glu Ser Val Arg Gly Arg Phe Thr Ile Ser Arg Asp Asp Ser Lys
 65                  70                  75 aac agc ctg tat ctg cag atg aac agc ctg aaa acc gaa gat acc gcg      287
Asn Ser Leu Tyr Leu Gln Met Asn Ser Leu Lys Thr Glu Asp Thr Ala
 80                  85                  90                  95 gtg tat tat tgc tgc cgt acc ccg tgg gtg tat gcg atg gat tgc tgg      335
Val Tyr Tyr Cys Cys Arg Thr Pro Trp Val Tyr Ala Met Asp Cys Trp
                100                 105                 110 ggc cag ggc acc ctg gtg acc gtg agc agc ggc ggc ggc gga agc ggc      383
Gly Gln Gly Thr Leu Val Thr Val Ser Ser Gly Gly Gly Gly Ser Gly
            115                 120                 125 ggt ggc ggc agc tgc ggc ggc ggc agc gac att gtg ctg acc cag          431
Gly Gly Gly Ser Cys Gly Gly Gly Ser Asp Ile Val Leu Thr Gln
        130                 135                 140 agc ccg gat agc ctg gcg gtg agc ctg ggc gaa cgt gcg acc att aac      479
Ser Pro Asp Ser Leu Ala Val Ser Leu Gly Glu Arg Ala Thr Ile Asn
            145                 150                 155
```

```
tgc cgt gcg agc aaa agc gtg agc gcg agc ggc tat att tat atg cat      527
Cys Arg Ala Ser Lys Ser Val Ser Ala Ser Gly Tyr Ile Tyr Met His
160             165                 170                 175 tgg tat cag cag aaa ccg ggc cag ccg ccg aaa ctg ctg att agc ctg      575
Trp Tyr Gln Gln Lys Pro Gly Gln Pro Pro Lys Leu Leu Ile Ser Leu
                180                 185                 190 gcg agc aac ctg gaa agc ggc gtg ccg gat cgt ttt agc ggc agc ggc      623
Ala Ser Asn Leu Glu Ser Gly Val Pro Asp Arg Phe Ser Gly Ser Gly
            195                 200                 205 agc ggc acc gat ttt acc ctg acc att agc agc ctg cag gcg gaa gat      671
Ser Gly Thr Asp Phe Thr Leu Thr Ile Ser Ser Leu Gln Ala Glu Asp
        210                 215                 220 gtg gcg gtg tat tat tgc cag cat agc cgt gaa ctg ccg ctg acc ttt      719
Val Ala Val Tyr Tyr Cys Gln His Ser Arg Glu Leu Pro Leu Thr Phe
    225                 230                 235 ggc ggc ggc acc aaa gtg gaa att aaa cat cat cat cat cat cat taa      767
Gly Gly Gly Thr Lys Val Glu Ile Lys His His His His His His
240                 245                 250 ggatcc                                                                773

<210> SEQ ID NO 16
<211> LENGTH: 254
<212> TYPE: PRT
<213> ORGANISM: Artificial Sequence
<220> FEATURE:
<223> OTHER INFORMATION: Synthetic Construct

<400> SEQUENCE: 16

Met Glu Val Gln Leu Val Glu Ser Gly Gly Gly Leu Val Gln Pro Gly
1               5                   10                  15

Gly Ser Leu Arg Leu Ser Cys Ala Thr Ser Gly Phe Thr Phe Ser Asn
            20                  25                  30

Tyr Arg Met His Trp Leu Arg Gln Ala Pro Gly Lys Gly Leu Glu Trp
        35                  40                  45

Ile Gly Val Ile Thr Val Lys Ser Asp Asn Tyr Gly Ala Lys Tyr Ala
    50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
                85                  90                  95

Tyr Tyr Cys Cys Arg Thr Pro Trp Val Tyr Ala Met Asp Cys Trp Gly
            100                 105                 110

Gln Gly Thr Leu Val Thr Val Ser Gly Gly Gly Ser Gly Gly Gly Gly
        115                 120                 125

Gly Gly Ser Cys Gly Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
                165                 170                 175

Tyr Gln Gln Lys Pro Gly Gln Pro Pro Lys Leu Leu Ile Ser Leu Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln His Ser Arg Glu Leu Pro Leu Thr Phe Gly
225                 230                 235                 240
```

Gly Gly Thr Lys Val Glu Ile Lys His His His His His His
                245                 250

<210> SEQ ID NO 17
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 17

```
cc atg gaa gtg cag ctg gtg gaa agc ggc ggc ggc ctg gtg cag ccg         47
   Met Glu Val Gln Leu Val Glu Ser Gly Gly Gly Leu Val Gln Pro
   1               5                   10                  15 ggc ggc agc ctg cgt ctg agc tgc gcg gcg agc ggc ttt acc ttt agc        95
Gly Gly Ser Leu Arg Leu Ser Cys Ala Ala Ser Gly Phe Thr Phe Ser
            20                  25                  30 aac tat cgt atg cat tgg gtg cgt cag gcg ccg ggc aaa ggc ctg gaa       143
Asn Tyr Arg Met His Trp Val Arg Gln Ala Pro Gly Lys Gly Leu Glu
        35                  40                  45 tgg gtg ggc gtg att acc gtg aaa agc gat aac tat ggc gcg aaa tat       191
Trp Val Gly Val Ile Thr Val Lys Ser Asp Asn Tyr Gly Ala Lys Tyr
    50                  55                  60 gcg gaa agc gtg cgt ggc cgt ttt acc att agc cgt gat gat agc aaa       239
Ala Glu Ser Val Arg Gly Arg Phe Thr Ile Ser Arg Asp Asp Ser Lys
65                  70                  75                  80 aac agc ctg tat ctg cag atg aac agc ctg aaa acc gaa gat acc gcg       287
Asn Ser Leu Tyr Leu Gln Met Asn Ser Leu Lys Thr Glu Asp Thr Ala
                85                  90                  95 gtg tat tat tgc gcg cgt acc ccg tgg gtg tat gcg atg gat tgc tgg       335
Val Tyr Tyr Cys Ala Arg Thr Pro Trp Val Tyr Ala Met Asp Cys Trp
            100                 105                 110 ggc cag ggc acc ctg gtg acc gtg agc agc ggc ggc ggc gga agc ggc       383
Gly Gln Gly Thr Leu Val Thr Val Ser Ser Gly Gly Gly Gly Ser Gly
        115                 120                 125 ggt ggc ggc agc tgc ggc ggc ggc agc aac att gtg ctg acc cag           431
Gly Gly Gly Ser Cys Gly Gly Gly Ser Asn Ile Val Leu Thr Gln
    130                 135                 140 agc ccg gat agc ctg gcg gtg agc ctg ggc gaa cgt gcg acc att aac       479
Ser Pro Asp Ser Leu Ala Val Ser Leu Gly Glu Arg Ala Thr Ile Asn
145                 150                 155 tgc cgt gcg agc aaa agc gtg agc gcg agc ggc tat att tat atg cat       527
Cys Arg Ala Ser Lys Ser Val Ser Ala Ser Gly Tyr Ile Tyr Met His
160                 165                 170                 175 tgg tat cag cag aaa ccg ggc cag ccg ccg aaa ctg ctg att agc ctg       575
Trp Tyr Gln Gln Lys Pro Gly Gln Pro Pro Lys Leu Leu Ile Ser Leu
            180                 185                 190 gcg agc aac ctg gaa agc ggc gtg ccg gat cgt ttt agc ggc agc ggc       623
Ala Ser Asn Leu Glu Ser Gly Val Pro Asp Arg Phe Ser Gly Ser Gly
        195                 200                 205 agc ggc acc gat ttt acc ctg acc att agc agc ctg cag gcg gaa gat       671
Ser Gly Thr Asp Phe Thr Leu Thr Ile Ser Ser Leu Gln Ala Glu Asp
    210                 215                 220 gtg gcg gtg tat tat tgc cag cat agc cgt gaa ctg ccg ctg acc ttt       719
Val Ala Val Tyr Tyr Cys Gln His Ser Arg Glu Leu Pro Leu Thr Phe
225                 230                 235 ggc ggc ggc acc aaa gtg gaa att aaa cat cat cat cat cat cat taa       767
Gly Gly Gly Thr Lys Val Glu Ile Lys His His His His His His
240                 245                 250
```

```
                                              -continued ggatcc                                                                        773

<210> SEQ ID NO 18
<211> LENGTH: 254
<212> TYPE: PRT
<213> ORGANISM: Artificial Sequence
<220> FEATURE:
<223> OTHER INFORMATION: Synthetic Construct

<400> SEQUENCE: 18

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Asn
            20                  25                  30

Tyr Arg Met His Trp Val Arg Gln Ala Pro Gly Lys Gly Leu Glu Trp
        35                  40                  45

Val Gly Val Ile Thr Val Lys Ser Asp Asn Tyr Gly Ala Lys Tyr Ala
    50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
                85                  90                  95

Tyr Tyr Cys Ala Arg Thr Pro Trp Val Tyr Ala Met Asp Cys Trp Gly
            100                 105                 110

Gln Gly Thr Leu Val Thr Val Ser Ser Gly Gly Gly Ser Gly Gly
        115                 120                 125

Gly Gly Ser Cys Gly Gly Gly Ser Asn Ile Val Leu Thr Gln Ser
    130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
                165                 170                 175

Tyr Gln Gln Lys Pro Gly Gln Pro Pro Lys Leu Leu Ile Ser Leu Ala
            180                 185                 190

Ser Asn Leu Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln His Ser Arg Glu Leu Pro Leu Thr Phe Gly
225                 230                 235                 240

Gly Gly Thr Lys Val Glu Ile Lys His His His His His His
                245                 250

<210> SEQ ID NO 19
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 19 cc atg gaa gtg cag ctg gtg gaa agc ggc ggc ggc ctg gtg cag ccg        47
   Met Glu Val Gln Leu Val Glu Ser Gly Gly Gly Leu Val Gln Pro
   1               5                   10                  15 ggc ggc agc ctg cgt ctg agc tgc gcg acc agc ggc ttt acc ttt agc       95
Gly Gly Ser Leu Arg Leu Ser Cys Ala Thr Ser Gly Phe Thr Phe Ser
```

-continued

```
                     20                  25                  30
aac tat cgt atg cat tgg gtg cgt cag gcg ccg ggc aaa ggc ctg gaa        143
Asn Tyr Arg Met His Trp Val Arg Gln Ala Pro Gly Lys Gly Leu Glu
             35                  40                  45 tgg att ggc gtg att acc gtg aaa agc gat aac tat ggc gcg aaa tat        191
Trp Ile Gly Val Ile Thr Val Lys Ser Asp Asn Tyr Gly Ala Lys Tyr
         50                  55                  60 gcg gaa agc gtg cgt ggc cgt ttt acc att agc cgt gat gat agc aaa        239
Ala Glu Ser Val Arg Gly Arg Phe Thr Ile Ser Arg Asp Asp Ser Lys
 65                  70                  75                  80 aac agc ctg tat ctg cag atg aac agc ctg aaa acc gaa gat acc gcg        287
Asn Ser Leu Tyr Leu Gln Met Asn Ser Leu Lys Thr Glu Asp Thr Ala
                 85                  90                  95 gtg tat tat tgc gcg cgt acc ccg tgg gtg tat gcg atg gat tgc tgg        335
Val Tyr Tyr Cys Ala Arg Thr Pro Trp Val Tyr Ala Met Asp Cys Trp
            100                 105                 110 ggc cag ggc acc ctg gtg acc gtg agc agc ggc ggc ggc gga agc ggc        383
Gly Gln Gly Thr Leu Val Thr Val Ser Ser Gly Gly Gly Gly Ser Gly
        115                 120                 125 ggt ggc ggc agc tgc ggc ggc ggc agc aac att gtg ctg acc cag            431
Gly Gly Gly Ser Cys Gly Gly Gly Ser Asn Ile Val Leu Thr Gln
130                 135                 140 agc ccg gat agc ctg gcg gtg agc ctg ggc gaa cgt gcg acc att aac        479
Ser Pro Asp Ser Leu Ala Val Ser Leu Gly Glu Arg Ala Thr Ile Asn
    145                 150                 155 tgc cgt gcg agc aaa agc gtg agc gcg agc ggc tat att tat atg cat        527
Cys Arg Ala Ser Lys Ser Val Ser Ala Ser Gly Tyr Ile Tyr Met His
160                 165                 170                 175 tgg tat cag cag aaa ccg ggc cag ccg ccg aaa ctg ctg att agc ctg        575
Trp Tyr Gln Gln Lys Pro Gly Gln Pro Pro Lys Leu Leu Ile Ser Leu
                180                 185                 190 gcg agc aac ctg gaa agc ggc gtg ccg gat cgt ttt agc ggc agc ggc        623
Ala Ser Asn Leu Glu Ser Gly Val Pro Asp Arg Phe Ser Gly Ser Gly
            195                 200                 205 agc ggc acc gat ttt acc ctg acc att agc agc ctg cag gcg gaa gat        671
Ser Gly Thr Asp Phe Thr Leu Thr Ile Ser Ser Leu Gln Ala Glu Asp
        210                 215                 220 gtg gcg gtg tat tat tgc cag cat agc cgt gaa ctg ccg ctg acc ttt        719
Val Ala Val Tyr Tyr Cys Gln His Ser Arg Glu Leu Pro Leu Thr Phe
225                 230                 235 ggc ggc ggc acc aaa gtg gaa att aaa cat cat cat cat cat cat taa        767
Gly Gly Gly Thr Lys Val Glu Ile Lys His His His His His His
240                 245                 250 ggatcc                                                                  773
```

<210> SEQ ID NO 20
<211> LENGTH: 254
<212> TYPE: PRT
<213> ORGANISM: Artificial Sequence
<220> FEATURE:
<223> OTHER INFORMATION: Synthetic Construct

<400> SEQUENCE: 20

```
Met Glu Val Gln Leu Val Glu Ser Gly Gly Gly Leu Val Gln Pro Gly
  1               5                  10                  15

Gly Ser Leu Arg Leu Ser Cys Ala Thr Ser Gly Phe Thr Phe Ser Asn
             20                  25                  30

Tyr Arg Met His Trp Val Arg Gln Ala Pro Gly Lys Gly Leu Glu Trp
         35                  40                  45

Ile Gly Val Ile Thr Val Lys Ser Asp Asn Tyr Gly Ala Lys Tyr Ala
```

|   |   |   |   |   |   |   |   |   |   |   |   |   |   |   |   |
|---|---|---|---|---|---|---|---|---|---|---|---|---|---|---|---|
|   |   | 50 |   |   |   | 55 |   |   |   |   | 60 |   |   |   |   |

Glu Ser Val Arg Gly Arg Phe Thr Ile Ser Arg Asp Asp Ser Lys Asn
65                       70                        75                        80

Ser Leu Tyr Leu Gln Met Asn Ser Leu Lys Thr Glu Asp Thr Ala Val
                85                        90                        95

Tyr Tyr Cys Ala Arg Thr Pro Trp Val Tyr Ala Met Asp Cys Trp Gly
                100                       105                       110

Gln Gly Thr Leu Val Thr Val Ser Ser Gly Gly Gly Ser Gly Gly
                115                       120                       125

Gly Gly Ser Cys Gly Gly Gly Ser Asn Ile Val Leu Thr Gln Ser
            130                       135                   140

Pro Asp Ser Leu Ala Val Ser Leu Gly Glu Arg Ala Thr Ile Asn Cys
145                       150                       155                       160

Arg Ala Ser Lys Ser Val Ser Ala Ser Gly Tyr Ile Tyr Met His Trp
                165                       170                       175

Tyr Gln Gln Lys Pro Gly Gln Pro Pro Lys Leu Leu Ile Ser Leu Ala
                180                       185                       190

Ser Asn Leu Glu Ser Gly Val Pro Asp Arg Phe Ser Gly Ser Gly Ser
                195                       200                       205

Gly Thr Asp Phe Thr Leu Thr Ile Ser Ser Leu Gln Ala Glu Asp Val
            210                       215                   220

Ala Val Tyr Tyr Cys Gln His Ser Arg Glu Leu Pro Leu Thr Phe Gly
225                       230                       235                       240

Gly Gly Thr Lys Val Glu Ile Lys His His His His His His
                245                       250

<210> SEQ ID NO 21
<211> LENGTH: 773
<212> TYPE: DNA
<213> ORGANISM: Artificial Sequence
<220> FEATURE:
<223> OTHER INFORMATION: Synthetic Peptide
<220> FEATURE:
<221> NAME/KEY: CDS
<222> LOCATION: (3)..(767)

<400> SEQUENCE: 21

```
cc atg gaa gtg cag ctg gtg gaa agc ggc ggc ggc ctg gtg cag ccg        47
   Met Glu Val Gln Leu Val Glu Ser Gly Gly Gly Leu Val Gln Pro
   1               5                   10                  15 ggc ggc agc ctg cgt ctg agc tgc gcg acc agc ggc ttt acc ttt agc        95
Gly Gly Ser Leu Arg Leu Ser Cys Ala Thr Ser Gly Phe Thr Phe Ser
                20                  25                  30 aac tat cgt atg cat tgg ctg cgt cag gcg ccg ggc aaa ggc ctg gaa       143
Asn Tyr Arg Met His Trp Leu Arg Gln Ala Pro Gly Lys Gly Leu Glu
            35                  40                  45 tgg att ggc gtg att acc gtg aaa agc gat aac tat ggc gcg aaa tat       191
Trp Ile Gly Val Ile Thr Val Lys Ser Asp Asn Tyr Gly Ala Lys Tyr
        50                  55                  60 gcg gaa agc gtg cgt ggc cgt ttt acc att agc cgt gat gat agc aaa       239
Ala Glu Ser Val Arg Gly Arg Phe Thr Ile Ser Arg Asp Asp Ser Lys
65                  70                  75 aac agc ctg tat ctg cag atg aac agc ctg aaa acc gaa gat acc gcg       287
Asn Ser Leu Tyr Leu Gln Met Asn Ser Leu Lys Thr Glu Asp Thr Ala
80                  85                  90                  95 gtg tat tat tgc gcg cgt acc ccg tgg gtg tat gcg atg gat tgc tgg       335
Val Tyr Tyr Cys Ala Arg Thr Pro Trp Val Tyr Ala Met Asp Cys Trp
                100                 105                 110 ggc cag ggc acc ctg gtg acc gtg agc agc ggc ggc ggc gga agc ggc       383
```

```
Gly Gln Gly Thr Leu Val Thr Val Ser Ser Gly Gly Gly Ser Gly
            115                 120                 125 ggt ggc ggc agc tgc ggc ggc ggc agc aac att gtg ctg acc cag    431
Gly Gly Gly Ser Cys Gly Gly Gly Ser Asn Ile Val Leu Thr Gln
        130                 135                 140 agc ccg gat agc ctg gcg gtg agc ctg ggc gaa cgt gcg acc att aac    479
Ser Pro Asp Ser Leu Ala Val Ser Leu Gly Glu Arg Ala Thr Ile Asn
    145                 150                 155 tgc cgt gcg agc aaa agc gtg agc gcg agc ggc tat att tat atg cat    527
Cys Arg Ala Ser Lys Ser Val Ser Ala Ser Gly Tyr Ile Tyr Met His
160                 165                 170                 175 tgg tat cag cag aaa ccg ggc cag ccg ccg aaa ctg ctg att agc ctg    575
Trp Tyr Gln Gln Lys Pro Gly Gln Pro Pro Lys Leu Leu Ile Ser Leu
                180                 185                 190 gcg agc aac ctg gaa agc ggc gtg ccg gat cgt ttt agc ggc agc ggc    623
Ala Ser Asn Leu Glu Ser Gly Val Pro Asp Arg Phe Ser Gly Ser Gly
            195                 200                 205 agc ggc acc gat ttt acc ctg acc att agc agc ctg cag gcg gaa gat    671
Ser Gly Thr Asp Phe Thr Leu Thr Ile Ser Ser Leu Gln Ala Glu Asp
        210                 215                 220 gtg gcg gtg tat tat tgc cag cat agc cgt gaa ctg ccg ctg acc ttt    719
Val Ala Val Tyr Tyr Cys Gln His Ser Arg Glu Leu Pro Leu Thr Phe
    225                 230                 235 ggc ggc ggc acc aaa gtg gaa att aaa cat cat cat cat cat cat taa    767
Gly Gly Gly Thr Lys Val Glu Ile Lys His His His His His His
240                 245                 250 ggatcc                                                              773

<210> SEQ ID NO 22
<211> LENGTH: 254
<212> TYPE: PRT
<213> ORGANISM: Artificial Sequence
<220> FEATURE:
<223> OTHER INFORMATION: Synthetic Construct

<400> SEQUENCE: 22

Met Glu Val Gln Leu Val Glu Ser Gly Gly Gly Leu Val Gln Pro Gly
1               5                   10                  15

Gly Ser Leu Arg Leu Ser Cys Ala Thr Ser Gly Phe Thr Phe Ser Asn
            20                  25                  30

Tyr Arg Met His Trp Leu Arg Gln Ala Pro Gly Lys Gly Leu Glu Trp
        35                  40                  45

Ile Gly Val Ile Thr Val Lys Ser Asp Asn Tyr Gly Ala Lys Tyr Ala
    50                  55                  60

Glu Ser Val Arg Gly Arg Phe Thr Ile Ser Arg Asp Asp Ser Lys Asn
65                  70                  75                  80

Ser Leu Tyr Leu Gln Met Asn Ser Leu Lys Thr Glu Asp Thr Ala Val
            85                  90                  95

Tyr Tyr Cys Cys Arg Thr Pro Trp Val Tyr Ala Met Asp Cys Trp Gly
        100                 105                 110

Gln Gly Thr Leu Val Thr Val Ser Ser Gly Gly Gly Ser Gly Gly
    115                 120                 125

Gly Gly Ser Cys Gly Gly Gly Ser Asn Ile Val Leu Thr Gln Ser
130                 135                 140

Pro Asp Ser Leu Ala Val Ser Leu Gly Glu Arg Ala Thr Ile Asn Cys
145                 150                 155                 160

Arg Ala Ser Lys Ser Val Ser Ala Ser Gly Tyr Ile Tyr Met His Trp
            165                 170                 175
```

```
Tyr Gln Gln Lys Pro Gly Gln Pro Pro Lys Leu Leu Ile Ser Leu Ala
            180                 185                 190

Ser Asn Leu Glu Ser Gly Val Pro Asp Arg Phe Ser Gly Ser Gly Ser
            195                 200                 205

Gly Thr Asp Phe Thr Leu Thr Ile Ser Ser Leu Gln Ala Glu Asp Val
            210                 215                 220

Ala Val Tyr Tyr Cys Gln His Ser Arg Glu Leu Pro Leu Thr Phe Gly
225                 230                 235                 240

Gly Gly Thr Lys Val Glu Ile Lys His His His His His
            245                 250
```

<210> SEQ ID NO 23
<211> LENGTH: 126
<212> TYPE: PRT
<213> ORGANISM: Artificial Sequence
<220> FEATURE:
<223> OTHER INFORMATION: Synthetic Peptide

<400> SEQUENCE: 23

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Gly Asn Lys Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asn Tyr Tyr Gly Ser Thr Trp Tyr Phe Asp Val Trp
            100                 105                 110

Gly Ala Gly Thr Thr Val Thr Val Ser Ser Glu Ser Ala Arg
            115                 120                 125
```

<210> SEQ ID NO 24
<211> LENGTH: 125
<212> TYPE: PRT
<213> ORGANISM: Murine

<400> SEQUENCE: 24

```
Glu Val Gln Val Val Glu Thr Gly Gly Gly Leu Val Arg Pro Gly Asn
1               5                   10                  15

Ser Leu Lys Leu Ser Cys Leu Thr Ser Gly Phe Thr Phe Ser Asn Tyr
            20                  25                  30

Arg Met His Trp Leu Arg Gln Pro Pro Gly Lys Arg Leu Glu Trp Ile
        35                  40                  45

Ala Val Ile Thr Val Lys Ser Asp Asn Tyr Gly Ala Lys Tyr Ala Glu
    50                  55                  60

Ser Val Arg Gly Arg Phe Thr Ile Ser Arg Asp Asp Ser Lys Ser Ser
65                  70                  75                  80

Val Tyr Leu Gln Met Asn Arg Leu Arg Glu Glu Asp Thr Ala Thr Tyr
                85                  90                  95

Tyr Cys Cys Arg Thr Pro Trp Val Tyr Ala Met Asp Cys Trp Gly Gln
            100                 105                 110

Gly Thr Ser Val Ile Val Ser Ser Ala Lys Thr Thr Pro
            115                 120                 125
```

<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 25

Gly Gly Gly Gly Ser Gly Gly Gly Ser Cys Gly Gly Gly Ser
1               5                   10                  15

<210> SEQ ID NO 26
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 26

Asp Ile Val Met Thr Gln Ser Pro Ser Ser Leu Ser Val Ser Ala Gly
1               5                   10                  15

Glu Arg Val Thr Met Ser Cys Lys Ser Ser Gln Ser Leu Leu Asn Ser
            20                  25                  30

Gly Asn Gln Lys Asn Phe Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Ile
            100                 105                 110

Lys Arg Ala Asp Ala Ala
        115

<210> SEQ ID NO 27
<211> LENGTH: 111
<212> TYPE: PRT
<213> ORGANISM: Murine

<400> SEQUENCE: 27

Asn Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
            20                  25                  30

Gly Tyr Ile Tyr Met His Trp Tyr Gln Gln Lys Pro Gly Gln Pro Pro
        35                  40                  45

Lys Leu Leu Ile Ser Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 28
<211> LENGTH: 110

```
<212> TYPE: PRT
<213> ORGANISM: Artificial Sequence
<220> FEATURE:
<223> OTHER INFORMATION: Synthetic Peptide

<400> SEQUENCE: 28

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ser
            20                  25                  30

Gly Tyr Ile Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Leu Thr Phe Gly Gly Gly Thr Lys Val Glu Ile
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 29

Asn Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
            20                  25                  30

Gly Tyr Ile Tyr Met His Trp Tyr Gln Gln Lys Pro Gly Gln Pro Pro
        35                  40                  45

Lys Leu Leu Ile Ser Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Ser Arg
                85                  90                  95

Glu Leu Pro Leu Thr Phe Gly Ala Gly Thr Lys Leu Glu Leu
            100                 105                 110

<210> SEQ ID NO 30
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 30

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ser
            20                  25                  30

Gly Tyr Ile Tyr Met His Trp Tyr Gln Gln Lys Pro Gly Gln Pro Pro
        35                  40                  45

Lys Leu Leu Ile Ser Leu Ala Ser Asn Leu Glu Ser Gly Val Pro Asp
    50                  55                  60
```

```
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Leu Thr Phe Gly Gly Gly Thr Lys Val Glu Ile
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 31

Asn Ile Val Leu Thr Gln Ser Pro Asp Ser Leu Ala Val Ser Leu Gly
 1               5                  10                  15

Glu Arg Ala Thr Ile Asn Cys Arg Ala Ser Lys Ser Val Ser Ala Ser
             20                  25                  30

Gly Tyr Ile Tyr Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Leu Thr Phe Gly Gly Gly Thr Lys Val Glu Ile
            100                 105                 110

<210> SEQ ID NO 32
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 32

Glu Val Gln Leu Val Glu Thr Gly Gly Gly Leu Val Arg Pro Gly Asn
 1               5                  10                  15

Ser Leu Lys Leu Ser Cys Leu Thr Ser Gly Phe Thr Phe Ser Asn Tyr
             20                  25                  30

Arg Met His Trp Leu Arg Gln Pro Pro Gly Lys Arg Leu Glu Trp Ile
         35                  40                  45

Ala Val Ile Thr Val Lys Ser Asp Asn Tyr Gly Ala Lys Tyr Ala Glu
 50                  55                  60

Ser Val Arg Gly Arg Phe Thr Ile Ser Arg Asp Asp Ser Lys Ser Ser
 65                  70                  75                  80

Val Tyr Leu Gln Met Asn Arg Leu Arg Glu Glu Asp Thr Ala Thr Tyr
                 85                  90                  95

Tyr Cys Cys Arg Thr Pro Trp Val Tyr Ala Met Asp Cys Trp Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Artificial Sequence
```

<220> FEATURE:
<223> OTHER INFORMATION: Synthetic Peptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Arg Met His Trp Val Arg Gln Ala Pro Gly Lys Gly Leu Glu Trp Val
        35                  40                  45

Gly Val Ile Thr Val Lys Ser Asp Asn Tyr Gly Ala Lys Tyr Ala Glu
    50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Thr Pro Trp Val Tyr Ala Met Asp Cys Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asn Tyr
            20                  25                  30

Arg Met His Trp Val Arg Gln Ala Pro Gly Lys Gly Leu Glu Trp Ile
        35                  40                  45

Gly Val Ile Thr Val Lys Ser Asp Asn Tyr Gly Ala Lys Tyr Ala Glu
    50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Thr Pro Trp Val Tyr Ala Met Asp Cys Trp Gly Gln
            100                 105                 110

Gly Thr Leu Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asn Tyr
            20                  25                  30

Arg Met His Trp Leu Arg Gln Ala Pro Gly Lys Gly Leu Glu Trp Ile

```
                    35                  40                  45
Gly Val Ile Thr Val Lys Ser Asp Asn Tyr Gly Ala Lys Tyr Ala Glu
        50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Cys Arg Thr Pro Trp Val Tyr Ala Met Asp Cys Trp Gly Gln
            100                 105                 110

Gly Thr Leu Val Thr Val Ser Ser
        115                 120

<210> SEQ ID NO 36
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 36

Gly Ser Gly Ser Gly Ser Cys Gly Ser Gly Ser Gly
1               5                   10
```

COMPOSITION AND METHOD FOR CANCER TREATMENT

CONTINUING APPLICATION DATA

This application claims priority to U.S. provisional application Ser. No. 60/557,258, filed on Mar. 27, 2004, and incorporated herein by reference.

STATEMENT REGARDING FEDERALLY FUNDED RESEARCH

The invention described herein was funded by NIH/NCI Grant No. P50 CA95060. The government may have certain rights to this invention.

BACKGROUND OF THE INVENTION

1. Field of the Invention

The invention relates to anti-CEACAM6 antibodies and antibody fragments, nucleic acids encoding them, methods of their manufacture, and methods to treat cancer using these compounds.

2. Description of the Background

CEACAM6, carcinoembryonic antigen cell adhesion molecule 6 or CD66, is related to carcinoembryonic antigen (CEA) and both are members of the immunoglobulin superfamily of proteins. CEACAM6 is a cell surface oncogene which is composed of immunoglobulin-like (Ig-like) domains capable of homophilic and heterophilic interactions (Beauchemin N, et. al., *Exp Cell Res.* 252(2): 243-9, 1999; Kuroki, et. al. *J Leukoc Biol.* 70(4): 543-50, 2001). It is a 320 amino acid long cell surface GPI-linked glycoprotein comprised of 3 Ig-like C2 domains with a short C-terminal cytoplasmic tail. The expression profile of CEACAM6 in normal human tissues show moderate expression in a variety of epithelial tissue and myeloid cells. However, deregulated cell surface expression of CEA and CEACAM6 is observed in approximately 50% human cancers (25). An immunohistochemical study of human tissue expression of CEACAM6 showed intense staining on proliferating cells of hyperplastic polyps and adenomas when compared to normal colorectal mucosa (26). These observations represent some of the earliest molecular events in colonic epithelial cells that lead to colorectal cancer. However, deregulated cell surface expression of CEACAM6 is observed in ~50% of human cancers, including colorectal and pancreatic cancer. Further, it has been demonstrated that de-regulated over-expression of CEACAM6 inhibits differentiation and apoptosis of cells when deprived of their anchorage to the extracellular matrix (ECM) (Ordoñez, et. al, *Cancer Research*, 60, 3419-3424, 2000), a process known as anoikis, which accompanies malignant transformation and strongly implicates CEACAM6 as an oncogene.

The utilization of therapeutic monoclonal antibodies (unconjugate or conjugated) for the treatment of human diseases including solid and hematological malignancies is well validated and established. Particularly useful for therapeutic applications are chimeric or humanized monoclonal antibodies due to their reduced immunological side effects. The efficacy and potency of this approach has been validated for Non-Hodgkin's Lymphoma (targeting CD20 antigen with rituximab) and breast cancer (targeting Her-2/Neu with Herceptin) with complete responses observed in patients with advanced stage disease.

Thus, there is an urgent need for novel therapies that specifically target up-regulated oncogenes such as CEACAM6.

SUMMARY OF THE INVENTION

The present invention provides high affinity antibodies and antibody fragments to CEACAM6. As used herein, the term antibody refers to a full length, complete antibody molecule as recognized in the art. The term fragment in the context of the present application refers to a portion of an antibody that retains the capability to bind to CEACAM6 with high affinity and specificity. Antibody fragments can be defined based on how many domains are included and/or excluded from the original full domain structure. Hence fragment can mean Variable heavy (VH) or Variable light (VL) or Single chain Fv (VH-VL) or Fab (VL-CL-VH-CH1) or Fab2 (VL-CL-VH-CH1)$_2$ or any of the above linked to novel small molecules, PEG or other protein domain(s) or labeling agents (fluorescent dye). A preferred example of such a fragment is a single chain antibody variable region fragment (ScFv). The term as used herein antibody generally refers to complete antibody molecules or fragments, unless there is a statement to the contrary.

These antibodies are preferably humanized or chimeric or ScFv (murine or humanized) antibodies or fragments. The antibodies and fragments of this invention are further provided as a pharmaceutical preparation for therapeutic use. The invention further provides recombinant DNA molecules encoding humanized CEACAM6 antibodies and expression systems for producing or manufacturing the antibodies recombinantly.

The anti-CEACAM6 antibodies of this invention are useful for treating conditions in which CEACAM6 is over-expressed, such as cancer. The antibodies act through a specific high affinity interaction at the cell surface to induce apoptosis and cell kill by antibody dependent cellular cytotoxicity (ADCC) and complement dependent cytotoxicity (CDC). In one embodiment, the applicant has developed humanized monoclonal antibodies, targeting CEACAM6. The applicant demonstrates the efficacy and potency of high affinity anti-CEACAM6 antibodies in cell killing assays described herein. As a further embodiment, applicant has utilized a structure based design algorithm for developing humanized antibodies that have been expressed in *E. coli.*

This invention provides a therapeutic method of administering an effective amount of anti-CEACAM6 antibodies to a patient that suffers from a disease in which CEACAM6 is overexpressed, such as cancer, particularly cancer of epithelial or myeloid origin. Cancers in which CEACAM6 is overexpressed include gastrointestinal cancers, including colorectal, pancreatic, stomach and others; lung cancer, breast cancer, leukemias, including acute myeloid leukemias; female reproductive cancers such as cervical, uterine and ovarian cancers; other epithelial cancers such as brain, prostate, liver and kidney tumors. Applicant has discovered that the known murine anti-CEACAM6 monoclonal antibody, 13.1, promotes pancreatic cancer cell apoptosis in tissue culture and may be used for therapeutic indications.

Thus, the present invention provides a method of treating cancer, comprising administering an effective amount of an anti-CEACAM6 antibody or antibody fragment to a patient in need thereof.

In one embodiment, the antibody or antibody fragment is humanized.

In another embodiment, the antibody or antibody fragment is chimeric.

In another embodiment, the antibody or antibody fragment is an ScFv.

In another embodiment, the ScFv is murine or humanized.

In another embodiment of the invention, the cancer is of epithelial or myeloid origin.

In one embodiment, the cancer is at least one selected from the group consisting of gastrointestinal cancer, lung cancer, breast cancer, leukemias, cervical cancer, uterine cancer, ovarian cancers, brain cancer, prostate cancer, liver cancer and kidney cancer.

In yet another embodiment, the cancer may be colorectal cancer, pancreatic cancer, stomach cancer and acute myeloid leukemia.

In another embodiment, the patient is a human or a non-human animal.

In another embodiment, the antibody or antibody fragment is administered parenterally, intraperitoneally intravenously or subcutaneous, orally, nasally, via inhalation or rectally.

In another embodiment, the antibody or antibody fragment is administered intravenously at a dosage of from 5 mg/m$^2$ to 2000 mg/m$^2$.

The present invention also provides a method of inducing apoptosis in cells expressing CEACAM6, comprising contacting the cells with an effective amount of an anti-CEACAM6 antibody or antibody fragment. Preferred embodiments are as described above. In another embodiment, the cells are cancer cells.

The present invention also provides a humanized murine anti-CEACAM6 antibody or antibody fragment. In a preferred embodiment, the antibody or antibody fragment contains the CDRs of monoclonal antibody 13.1. In another embodiment, the antibody or antibody fragment is modified with PEG.

The present invention also provides an anti-CEACAM6 ScFv. In a preferred embodiment, the ScFv contains the CDRs of monoclonal antibody 13.1. In another embodiment, the ScFv is modified with PEG.

The present invention also provides a fragment of an anti-CEACAM6 antibody which has high affinity for CEACAM6. In a preferred embodiment, the fragment contains the CDRs of monoclonal antibody 13.1. In another embodiment, the fragment is modified with PEG.

The present invention also provides a conjugate in which the antibody or fragment described above is conjugated to at least one other moiety.

The present invention also provides a pharmaceutical composition, comprising the antibody or fragment as discussed above and at least one pharmaceutical excipient.

In one embodiment of the invention, the excipient is one or more of water, pH buffers, wetting agents, salts, reducing agents, sugars, glycerol, glycol, oils, preservatives and antimicrobials.

The present invention also provides an antibody or fragment as described above.

The present invention also provides a method of producing the antibody or fragment as described above, comprising transforming a host cell with a nucleic acid which encodes the antibody or antibody fragment and isolating the antibody or antibody fragment from the host cell.

The present invention also provides a method of diagnosing over-expression of CEACAM6, comprising:
contacting a sample from a subject with an anti-CEACAM6 antibody or antibody fragment;
determining whether a complex formed between the antibody or antibody fragment and CEACAM6; and
correlating the formation of the complex with over-expression of CEACAM6 in the subject, or
correlating the absence of the complex with no over-expression of CEACAM6 in the subject.

The present invention also provides a method of diagnosing cancer or hematological malignancy involving over-expression of CEACAM6, comprising:
contacting a sample from a subject with an anti-CEACAM6 antibody or antibody fragment;
determining whether a complex formed between the antibody or antibody fragment and CEACAM6; and
correlating the formation of the complex with the presence of a cancer or hematological malignancy involving over-expression of CEACAM6 in the subject, or
correlating the absence of the complex with the absence of a cancer or hematological malignancy involving over-expression of CEACAM6 in the subject.

In one embodiment, the antibody or antibody fragment is a monoclonal antibody.

In another embodiment, the antibody or antibody fragment is a murine antibody or a humanized antibody.

In another embodiment, the subject is human.

In another embodiment, the sample is a biopsy sample.

In another embodiment, the antibody or antibody fragment is humanized.

In another embodiment, the antibody or antibody fragment is chimeric.

In another embodiment, the antibody or antibody fragment is an ScFv.

In another embodiment, of the invention the ScFv is murine or humanized.

BRIEF DESCRIPTION OF THE DRAWINGS

The invention will be better understood from a reading of the following detailed description taken in conjunction with the drawings in which like reference designators are used to designate like elements, and in which:

FIG. 4 is a chart showing the structure based sequence alignment of the murine anti-CEACAM6 $V_H$ and $V_L$ chains with the $V_H$ and $V_L$ of 1 MCP (SEQ ID NO: 23 and 24);

FIG. 6 is a chart showing the humanization of the $V_L$ chain of murine anti-CEACAM6. An asterisk denotes a position at which all query sequences have the exact same amino acid (called sequence identity). Two dots denote a position in the sequence at which all analyzed sequences have amino acids that are chemically similar (i.e. all acidic or all non-polar; called sequence conservation). One dot denotes a weaker chemical similarity (weaker sequence conservation). No annotation denotes that no chemical similarity exists;

FIG. 7 is a chart showing the humanization of the VH chain of murine anti-CEACAM6 (SEQ ID NO: 26 and 27). An asterisk denotes a position at which all query sequences have the exact same amino acid (called sequence identity). Two dots denote a position in the sequence at which all analyzed sequences have amino acids that are chemically similar (i.e. all acidic or all non-polar; called sequence conservation). One dot denotes a weaker chemical similarity (weaker sequence conservation). No annotation denotes that no chemical similarity exists;

FIG. 11 is a Western blot analysis of cleaved human caspase-2 of HPAF-2 pancreatic cancer cells treated with anti-CEACAM6 Mab (1 µg/mL) (A). 0 hr and 6 hr (B). 0 hr, 24 hr, 48 hr and 72 hr. Cleaved caspase-2 migrates at ~34 kDa.

DETAILED DESCRIPTION OF THE INVENTION

Figure 1:
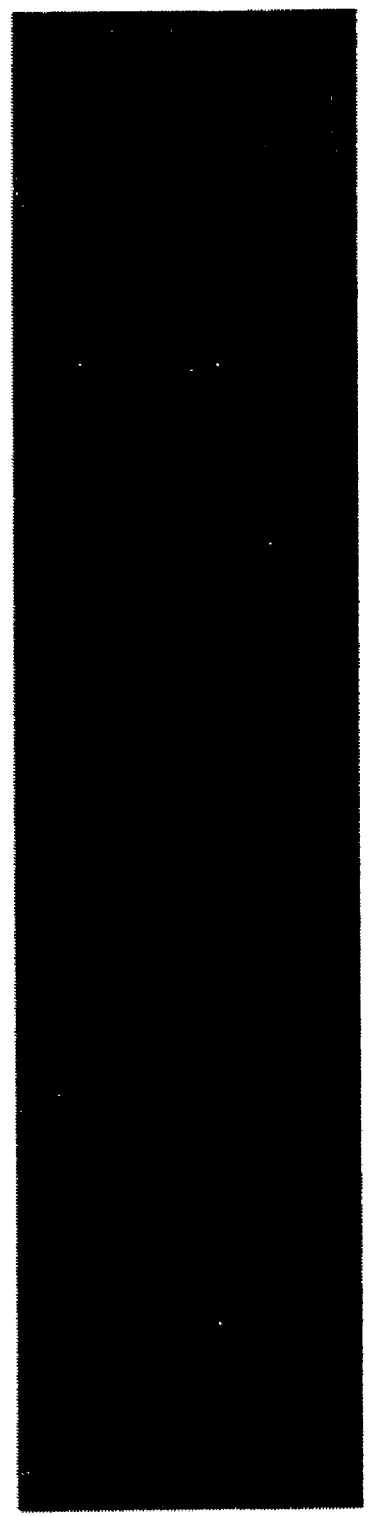
FIG. 1 is a Western blot showing the expression of CEACAM6 in 11 human pancreatic cancer cell lines, lanes from left to right are M: marker, 1: Capan-2, 2: CFPAC-1, 3: Panc-1, 4: ASPC-1, 5: MiaPaCa, 6: CaPan-1, 7: BXPC-3, 8: Hs766T, 9: su.86.86, 10: Mutj, 11: HPAF-2. The band at 45 kDa is an actin control.

Applicants have discovered that the CEACAM6 protein is a target for inducing apoptosis in cells over expressing CEACAM6 to cause cell death. Apoptosis is induced by treating such cells with antibodies that induce ADCC and CDC.

The humanized antibodies of the invention include intact immunoglobulin molecules, comprising 2 full-length heavy chains and 2 full-length light chains, for example, IgG, IgA, IgM, IgE, and IgD, and subsequences that induce apoptosis in cells overexpressing CEACAM6. Particular subsequences include, for example, single chain, such as ScFv, Fab, Fab' or (Fab) 2 fragment.

It was discovered that CEACAM6 overexpression in certain cells, such as cancerous cells, provides a therapeutic target. The recognition and binding of this target by high affinity antibodies leads to apoptosis or programmed cell death of the errant cells. Monoclonal antibodies which bind CEACAM6 and lead to apoptosis may be made by methods known in the art, such as first described by Kohler and Millstein (Kohler et al., 1975, Nature, 265:495-497.1, incorporated herein by reference). Humanized and chimeric antibodies may be made in various methods once the critical selection criteria are determined.

Humanization (also called Reshaping or Complementarity Determining Region—CDR grafing) is now a well-established technique for reducing the immunogenicity of monoclonal antibodies (Mab) from xenogeneic sources (commonly rodent) and for improving their activation of the human immune system. Although the mechanics of producing the engineered Mab using the techniques of molecular biology are relatively straightforward, simple grafting of the rodent CDRs into human frameworks does not always reconstitute the binding affinity and specificity of the original Mab. In order to humanize an antibody, the design is now the critical step in reproducing the function of the original molecule. This design includes various choices or selection criteria: the extents of the CDRs, the human frameworks to use and the substitution of residues from the rodent Mab into the human framework regions (backmutations). The positions of these backmutations have been identified principally by sequence/structural analysis or by analysis of a homology model of the variable regions' three-dimensional structure. Phage libraries can be used to vary the amino acids at chosen positions. Similarly, many approaches have been used to choose the most appropriate human frameworks in which to graft the rodent CDRs. One method may use a limited subset of well-characterized human Mabs (often where the structure is available), irrespective of the sequence identity to the rodent Mab (called the fixed-frameworks approach). One may use variable regions with high amino acid sequence identity to the rodent variable regions (homology matching or best-fit); others use consensus or germline sequences while still other methods select fragments of the framework sequences within each light or heavy chain variable region from several different human Mabs. Other approaches to humanization replace the surface rodent residues with the most common residues found in human Mabs ('resurfacing' or 'veneering').

One structure based method used to make humanized ScFv antibodies of this invention, providing the selection criteria is outlined below:

1. Sequence VL and VH regions (mouse anti-CEACAM6 Mab)
2. PSI-BLAST Search to identify Xtal structure of a mouse Mab with high sequence similarity to the VL and VH of anti-CEACAM Mab
3. Alignment of VL and VH 1MCP with VL and VH of anti-CEACAM6 (Clustal W)
4. Molecular modeling of CEACAM6 Mab VL and VH on 1 MCP (ICM 3.1, Sybyl 6.9)
5. Linking VL C-terminus to VH N-terminus
6. Identify a Human Acceptor for VL and VH (Human Anti-P53, 163.15)
7. Synthesize VL and VH with Gly-Ser containing or other Linker
8. Express DNA sequence and Purify antibodies In one embodiment, the humanized and/or chimeric antibodies of the invention comprise the CDRs, or consensus CDRs, of monoclonal antibody 13-1. The complete sequence of monoclonal antibody 13-1 is provided below:

```
Mouse monoclonal antibody 13-1 light
chain (SEQ ID NO: 1):
NIVLTQSPAS LAVSLGQRAT ISCRASKSVS ASGYIYMHWY
QQKPGQPPKL LISLASNLESGVPARFSGSG SGTDFTLNIH
PVEEEDVATY YCQHSRELPL TFGAGTKLEL
KRADAAPTVSIFPPPSSEQLT SGGASVVCFL NNFYPKDINV
KWKIDGSERQ NGVLNSWTDQ DSKDSTYSMSSTLTLTKDEY
ERHNSYTCEA THKTSTSPIV KSFNRNEC Mouse monoclonal antibody 13-1 heavy
chain (SEQ ID NO: 2):
EVQXVETGGG LVRPGNSLKL SCLTSGFTFS NYRMHWLRQP
PGKRLEWIAV ITVKSDNYGAKYAESVRGRF TISRDDSKSS
VYLQMNRLRE EDTATYYCCR TPWVYAMDCW
GQGTSVIVSSAKTTPPSVYP LAPGSAAQTN SMVTLGCLVK
GYFPEPVTVT WNSGSLSSGV HTFPAVLQSDLYTLSSSVTV
PSSTWPSETV TCNVAHPASS TKVDKKIVPR DCGCKPCICT
VPEVSSVFIFPPKPKDVLTI TLTPKVTCVV VDISKDDPEV
QFSWFVDDVE VHTAQTQPRE EQFNSTFRSVSELPIMHQDW
LNGKEFKCRV NSAAFPAPIE KTISKTKGRP KAPQVYTIPP
PKEQMAKDKVSLTCMITDFF PEDITVEWQW NGQPAENYKN
TQPIMDTDGS YFVYSKLNVQ KSNWEAGNTFTCSVLHEGLH
NHHTEKSLSH SPGK
```

See Akashi, S., Kato, K., Torizawa, T., Dohmae, N., Yamaguchi, H., Kamachi, M., Harada, A., Imanaka, T., Shimada, I. and Takio, K. Structural characterization of mouse monoclonal antibody 13-1 against a porphyrin derivative: identification of a disulfide bond in CDR-H3 of Mab 13-1. Biochem. Biophys. Res. Commun. 240 (3), 566-572 (1997), incorporated herein by reference.

Once the DNA sequence of the antibody molecule is obtained, it may be operably linked to promoters in suitable vectors for expression in a variety of hosts. Such vector-host systems are readily available from companies such as Promega or Invitrogen.

Useful cells for expression of the antibody encoding vectors to make protein are bacteria, such as E. coli, eukaryotic systems such as yeast or insect cells using a baculovirus system, or mammalian cells, such as CHO cells.

The murine and humanized antibody fragments may also be produced in COS cells, CHO cells, Multiple Myeloma cells and baculovirus u sing well established existing methods.

A wide variety of linker sequences may be used to link VL and VH, however incorporating amino acids with active groups such as sulfhydryl, such as cysteine, carboxyl, such as aspartic acid or glutamic acid, amines, such as lysine or arginine are useful for forming conjugates with other drugs, cytotoxic or detecting agents.

Useful 'high affinity' antibodies to CEACAM6 made by the methods described in this invention may be tested for cell killing activity or cytotoxicity in assays known in the art. One such assay is embodied by the method described in the example entitled Cellular Cytotoxicity Assay in the Examples provided herein. The method described herein also allows one to determine a qualitative concentration of antibodies to effect cell kill and thus be useful for treating cancer. Cancers for which anti-CEACAM6 antibodies may be useful include gastrointestinal cancers, including colorectal, pancreatic, stomach and others; lung cancer, breast cancer, leukemias, including acute myeloid leukemias; female reproductive cancers such as cervical, uterine and ovarian cancers; other epithelial cancers such as brain, prostate, liver and kidney tumors. Applicant has discovered that the known murine anti-CEACAM6 monoclonal antibody, 13.1, promotes pancreatic cancer cell apoptosis in tissue culture and may be used for such therapeutic indications.

The subject to be treated may be a human or a non-human animal. Preferably, the animal is a mammal. Examples of animals include dogs, cats, livestock and monkeys (e.g. Cyanomolgus).

"High affinity" as used to describe the antibodies of the present invention means anti-CEACAM6 antibodies which are capable of causing apoptosis of CEACAM6 bearing cells as determined by cytotoxic assays described and demonstrated in this application.

Monoclonal antibodies, particularly chimeric and humanized, obtained in this invention are useful for therapeutic indications. Such antibodies leading to cell death have $IC_{50}$ concentrations of 10 ng/ml-100 µg/ml, preferably 100 ng/ml-50 µg/ml and most preferably 1 µg/ml-20 µg/ml. Monoclonal anti-CEACAM6 antibodies, including humanized or chimeric, of the invention, particularly ScFv antibody fragments may have binding affinities of $10^{-10}$-$10^{-7}$ M, preferably $10^{-9}$-$10^{-8}$ M.

DNA microarray in combination with correlative RT-PCR, Northern and western blotting (these techniques being known to those of skill in the art) may be used to demonstrate overexpression of the tumor antigen CEACAM6 on human cancer cell lines to determine those tumors that may benefit from antibody therapy described herein. Those tumor tissues or cells over-expressing CEACAM6 two-fold or more compared to the same normal tissue or cells, preferably 5-fold or more, or most preferably 10-fold or more are most preferred for treatment with the anti-CEACAM6 antibodies. Further, immunohistochemical analysis of human cancer tissue utilizing an antibody targeting CEACAM6 can be used to determine overexpression, that is, increased expression in comparison to normal tissue.

The antibodies of the present invention may be given as a sole therapeutic agent or may be used in combination therapies. Other agents for combination therapy include Gemcitabine, 5-fluorouracil, irinotecan, cisplatin, oxaliplatin, EGF receptor monoclonal and VEGF monoclonal antibodies, hormonal therapy in prostate or reproductive cancer, doxorubicin, idarubicin, Ara-C, Mylotarg, carboplatin, taxotere, tyrosine kinase inhibitors (PDGFR, c-Kit, EGFR etc), as a conjugated antibody with radioactive ions (Iodine, Yttrium, etc); as a conjugated antibody with various toxins (Diphtheria, Psedomonas, others); as an antibody conjugated with any chemotherapy agent such as taxotere, doxorubicin or any of those recited above; as a conjugated antibody with protein kinase inhibitors and other signal transduction inhibitors/activators. Other conjugates may be made that are useful in detection or diagnostic indications, such as fluorescent or radioactive labels, biotin-avidin or streptavidin, reagents for conducting ELISA assays, MR agents such as Gadolinium, chelating moieties for chelating MR agents. Such diagnostic agents are known in the art and are useful for diagnosing disease, particularly cancer. Detection agents may be useful for research reagents as a detectable tag using optical means, such as fluorescent labeling, or radioactive labels.

The antibodies of the present invention may be prepared for pharmaceutical administration by methods and excipients generally known in the art (Remington's Pharmaceutical Sciences, E. W. Martin). Excipients may include water, pH buffers, such as citrate or phosphate buffers, 'wetting agents' such as Tweens or other detergents, salts such as sodium chloride, reducing agents such as thiols, sugars, such as dextrose, lactose, sucrose and the like, glycerol, glycol, oils, preservatives, antimicrobials, etc. The antibodies may be formulated in specialized delivery vehicles such as liposomes. The preparation may be prepared as a liquid, powder, solid or in gel form for administration. Administration may be via parenteral routes, such as intravenous, intraperitoneally or subcutaneous, oral, nasal, inhalation, rectally via suppositories or other known routes of administering drugs. Modifications of the anti-CEACAM6 antibody may be made to improve pharmacologic efficacy, such as PEGylation.

Dosages and administration schedules are readily determined by those skilled in the pharmacology. The antibodies of the invention may be administered intravenously from 5 mg/m$^2$ to 2000 mg/m$^2$, preferably 50 mg/m$^2$ to 1000 mg/m$^2$, most preferably 100 mg/m$^2$ to 500 mg/m$^2$.

The present invention also provides a method of diagnosing over-expression of CEACAM6, comprising:

contacting a sample from a subject with an anti-CEACAM6 antibody or antibody fragment;

determining whether a complex formed between the antibody or antibody fragment and CEACAM6; and correlating the formation of the complex with over-expression of CEACAM6 in the subject, or correlating the absence of the complex with no over-expression of CEACAM6 in the subject.

The present invention also provides a method of diagnosing cancer or hematological malignancy involving over-expression of CEACAM6, comprising:

contacting a sample from a subject with an anti-CEACAM6 antibody or antibody fragment;

determining whether a complex formed between the antibody or antibody fragment and CEACAM6; and correlating the formation of the complex with the presence of a cancer or hematological malignancy involving overexpression of CEACAM6 in the subject, or correlating the absence of the complex with the absence of a cancer or hematological malignancy involving over-expression of CEACAM6 in the subject.

Each of these methods is dependent on the formation of a detectable complex between the anti-CEACAM6 antibody or antibody fragment and CEACAM6, if it is present in the sample. If the complex forms in a detectable amount, the assay is positive. If the complex does not form in a detectable amount, the result is negative. Thus, these methods are similar to other well-known antibody assays which are widely used in medical diagnostics. The antibody can be fluorescently labeled for enhanced detection. Another method to detect CEACAM6 in a tumor would be to sequence the DNA of CEACAM6 after RT-PCR. This method successfully identifies the CEACAM6 message and any new mutations the tumor may have acquired during its evolution. This method has been utilized for EGFR mutations in non small cell lung cancer and BCR-Abl mutations in chronic myeloid leukemia. In a particularly preferred embodiment, the sample is a biopsy sample obtained using well-known clinical procedures. Examples of biopsy samples those obtained either by ultra sound guided endoscopy, CT guided biopsy of the tumor (Liver metastasis) or at surgery. The tissue is generally processed and embedded in paraffin or snap frozen for isolating RNA or DNA.

With respect to the amino acid and nucleic acid sequences described herein, the present invention also includes embodiments in which the amino acid or nucleic acid has at least 70%, 75%, preferably 80%, 85%, more preferably at least 90%, 95%, 97%, 98% or 99% identity or homology to the specific sequences described herein (see the Examples below). These nucleic acids will hybridize under stringent conditions to the complement of the nucleic acid sequences described herein. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995)), all incorporated herein by reference. Amino acid and polynucleotide identity, homology and/or similarity can be determined using the ClustalW algorithm, MEGA-LIGN*, Lasergene, Wis.).

EXAMPLES

The following Examples are provided to illustrate specific embodiments of the invention, and are not limiting in any way.

CEACAM6 Expression in Human Pancreatic Cancer Cell Lines

Three gene array-profiling studies on pancreatic cancer cell lines (11, 12, 13) and human pancreatic cancer biopsy samples (14, 15) have clearly shown that a number of genes are highly over-expressed. Of the highly over-expressed genes from these three studies, CEACAM6 had a 25-fold increase compared to normal pancreatic cells and was the number 1 expressed hit in one study (11).

DNA microarray in combination with correlative RT-PCR, Northern and western blotting are used to demonstrate overexpression of the tumor antigen CEACAM6 on several human pancreatic cancer cell lines. Further, immunchistochemical analysis utilizing a murine monoclonal antibody (Mab 13-1) targeting CEACAM6 on pancreatic cancer cell lines and pancreatic cancer patient biopsy specimens (25 of 30) have confirmed increased expression in comparison to normal pancreatic tissue.

Western Blotting

In this study, eleven human pancreatic cancer cell lines (Capan-2, CFPAC-1, Panc-1, ASPC-1, MiaPaCa-2, CaPan-1, BXPC-3, Hs766T, Su.86.86, Mutj and HPAF-2) were grown in tissue culture to confluence. Each of the cell lines were spun down, lysed in lysis buffer, run on SDS-PAGE, transferred to nitrocellulose and probed with the murine monoclonal antibody to CEACAM6 (13.1) and anti-actin antibody (control).

FIG. 1 shows a Western blot demonstrating the expression of CEACAM6 in eleven (11) human pancreatic cancer cell lines. The data of FIG. 1 includes the following cell lines: M-Marker, 1: Capan-2, 2: CFPAC-1, 3: Panc-1, 4: ASPC-1, 5: MiaPaCa-2, 6:, CaPan-1, 7: BXPC-3, 8: Hs766T, 9: Su.86.86, 10: Mutj, 11: HPAF-2. The band at 45 kDa is the actin control.

FIG. 1 shows that five (5) of the cell lines have a high level of expression of CEACAM6, namely cell lines CFPAC-1, ASPC-1, CaPan-1, BXPC-3 and HPAF-2. Two of those cell lines, namely lines Hs766T and Su.86.86, are low expressers, all migrating at a Mr 75kDa due to glycosylation.

Human Cancer Tissue Array

Thirty human pancreatic cancer patient biopsy samples were either deparaffinized and microwaved for antigen retrieval, or if fixed frozen, the above step was omitted. Both types of section were acetone fixed and stained with αNCA monoclonal antibody (13.1) and processed using a mixture of anti-Ms and anti-Rb immunoglobulins. After rinsing slides were incubated with Avidin-HRP reagent, rinsed and incubated in DAB. The slides were counter stained in hematoxylin. Of the 30 patient samples tested, 25 showed intense cell surface staining of neoplastic pancreatic duct cells. The surrounding normal tissue were not stained clearly delineating tumor cells from normal pancreas cells.

Figure 2:
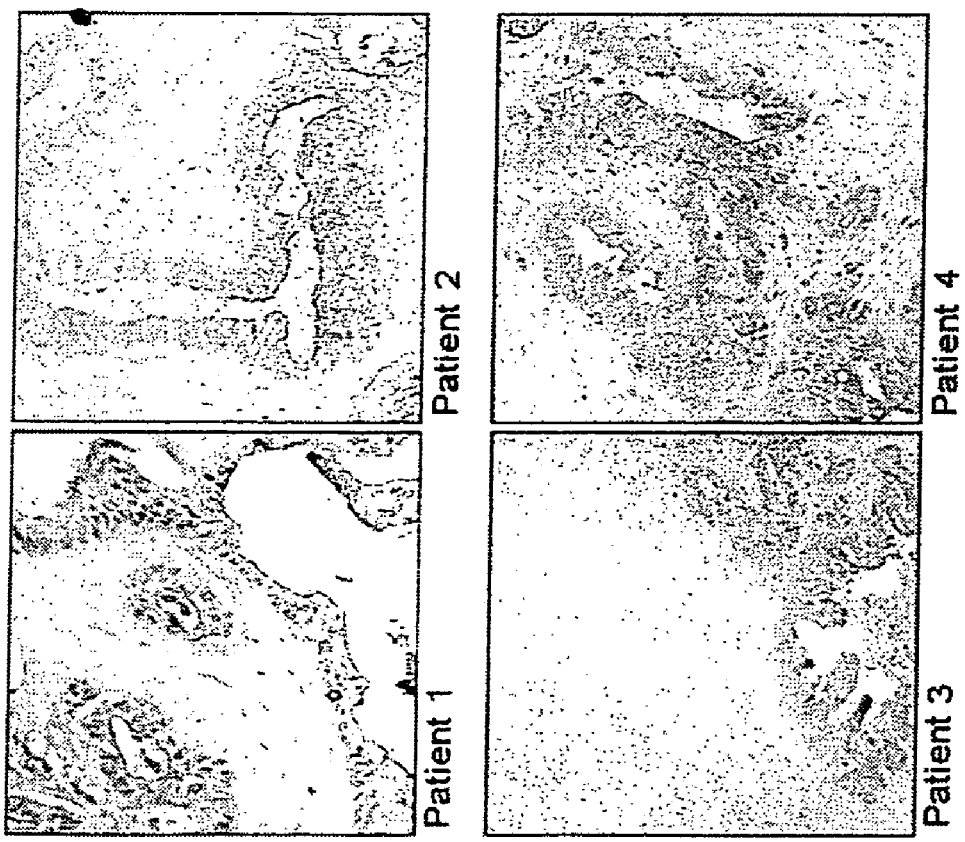
FIG. 2 shows immunohistochemical staining of four representative pancreatic adenocarcinoma patient biopsy samples.

FIG. 2 shows resulting immunohistochemical staining of four representative pancreatic adenocarcinoma patient biopsy samples with the murine anti-CEACAM6 monoclonal antibody. The intense dark brown staining of the malignant duct surface epithelium is evident.

Cellular Cytotoxicity Assay

To demonstrate that an anti-CEACAM-6 monoclonal antibody can mediate pancreatic cancer cell killing, Applicant has employed an in vitro cytotoxicity assay. This assay utilizes the CellTiter 96 Non-Radioactive Cell Proliferation Assay (Promega Corp., Madison, Wis.). MiaPaCa and HPAF-2 pancreatic cancer cells were plated in 0.1 mL medium on day 0 in 96-well microtiter plates (Falcon, #3072). On day 1, 10 µL, of serial dilutions of the commercially available anti-CEACAM-6 agent were added in replicates of 4 to the plates. After incubation for 4 days at 37° C. in a humidified incubator, 20 µL of a 20:1 mixture of [3-(4,5-dimethyl-2-yl)-5-(3 carboxymethoxyphenyl)-2-(4-sulfophenyl)-2H-tetrazolium, inner salt; MTS], 2 mg/ml, and an electron coupling reagent, phenazine methosulfate (PMS, 0.92 mg/ml in DPBS), was added to each well and incubated for 4 hours at 37° C. Absorbance was measured using Model 7520 microplate reader (Cambridge Technology, Inc.) at 490 nm.

Figure 3:
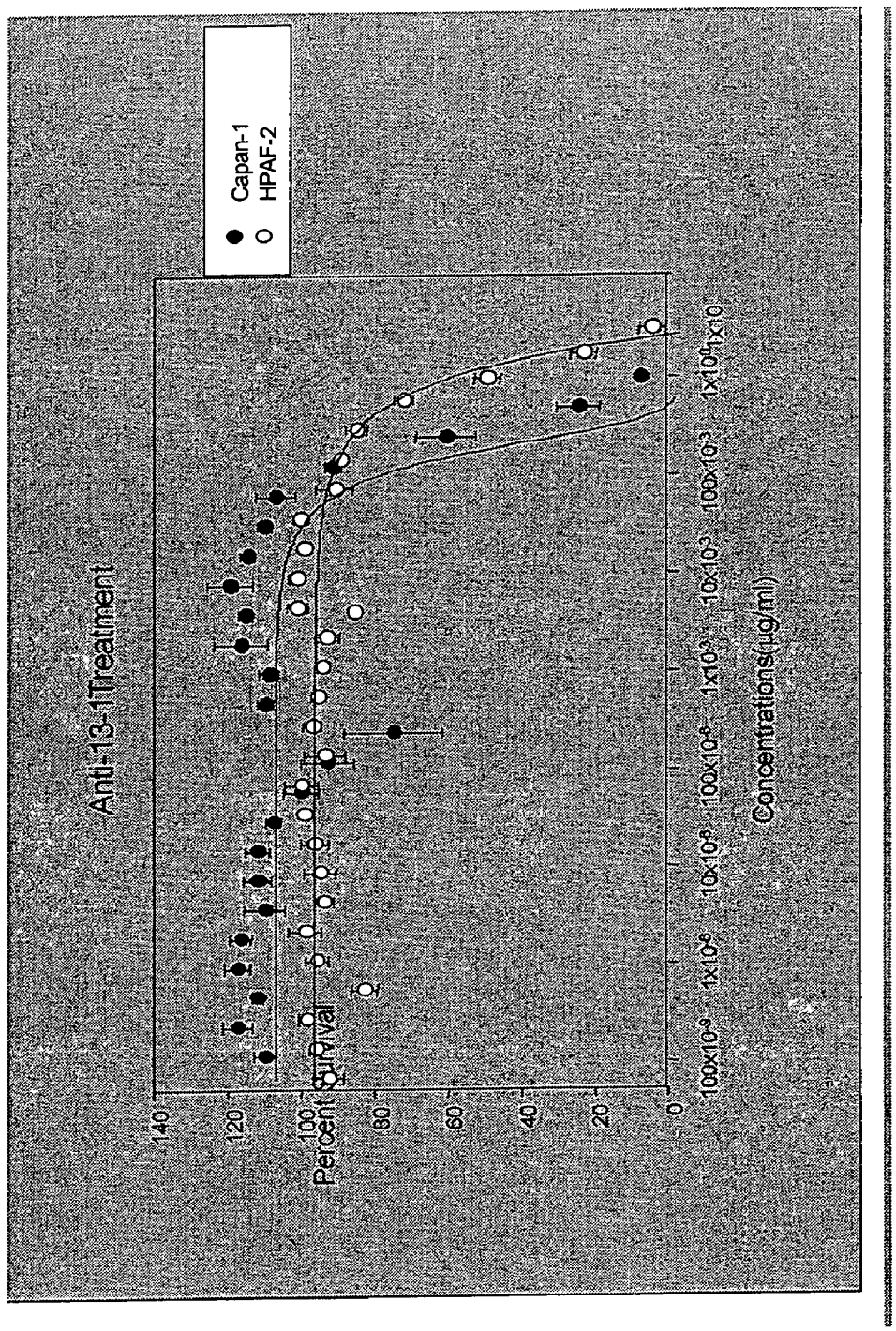
FIG. 3 is a graph showing the percent survival of two different pancreatic cancer cell lines in the presence of anti-CEACAM-6 monoclonal antibody.

FIG. 3 shows the percentage of survival of control calculated from the absorbance corrected for background absorbance. The surviving fraction of cells was determined by dividing the mean absorbance values of the monoclonal antibody by the mean absorbance values of the control. For the two pancreatic cancer cell lines evaluated, the mouse anti-CEACAM6 monoclonal antibody (13-1) promoted pancreatic cancer cell apoptosis with an $IC_{50}$=1-10 µg/ml. This is most likely due to inhibition of anoikis, a surveillance mechanism that prevents dysplasia and preserves normal tissue architecture. As those skilled in the art will appreciate, FIG. 3 shows that the anti-CEACAM-6 monoclonal antibody is efficient at cell killing in two different pancreatic cancer cell lines at a concentration of 1-10 µg/ml.

Humanization by Design

The mouse anti-CEACAM6 monoclonal antibody VL and VH region sequences were characterized by mass spectroscopic peptide mapping. The VL and VH sequences were identical to that in the NCBI protein sequence database. A PSI-BLAST search was used to identify a crystal structure of a mouse monoclonal antibody with the highest sequence similarity to the VL and VH of anti-CEACAM6 monoclonal antibody (13-1). The design cycle is shown in Table 1.

TABLE 1

Humanization By Structure-Based Design

| 1 | Sequence VL and VH regions (mouse anti-CEACAM6 Mab) |
| 2 | PSI-BLAST Search to identify Xtal structure of a mouse Mab with high sequence similarity to the VL and VH of anti-CEACAM Mab |
| 3 | Alignment of VL and VH 1 MCP with VL and VH of anti-CEACAM6 (Clustal W) |
| 4 | Molecular modeling of CEACAM6 Mab VL and VH on 1 MCP (ICM 3.1, Sybyl 6.9) |
| 5 | Linking VL C-terminus to VH N-terminus |
| 6 | Identify a Human Acceptor for VL and VH (Human Anti-P53, 163.15) |
| 7 | Synthesize VL and VH with Gly-Ser Linker |
| 8 | Express in and Purify from E. Coli |

Applicant identified the crystal structure of 1MCP, a mouse monoclonal antibody against phosphorylcholine, as the best structure for molecular modeling and extracted from the protein database. Referring to FIG. 4, sequence alignments of VL and VH domains of 1 MCP were performed with the VL and VH of anti-CEACAM6 using the program Clustal W. Molecular modeling of the anti-CEACAM6 monoclonal antibody VL and VH were performed using the crystal structure of 1MCP on an Octane Silicon Graphics workstation using the program ICM (Internal Coordinate Mechanism) and refined in Sybyl 6.9 (Tripos).

Figure 5:
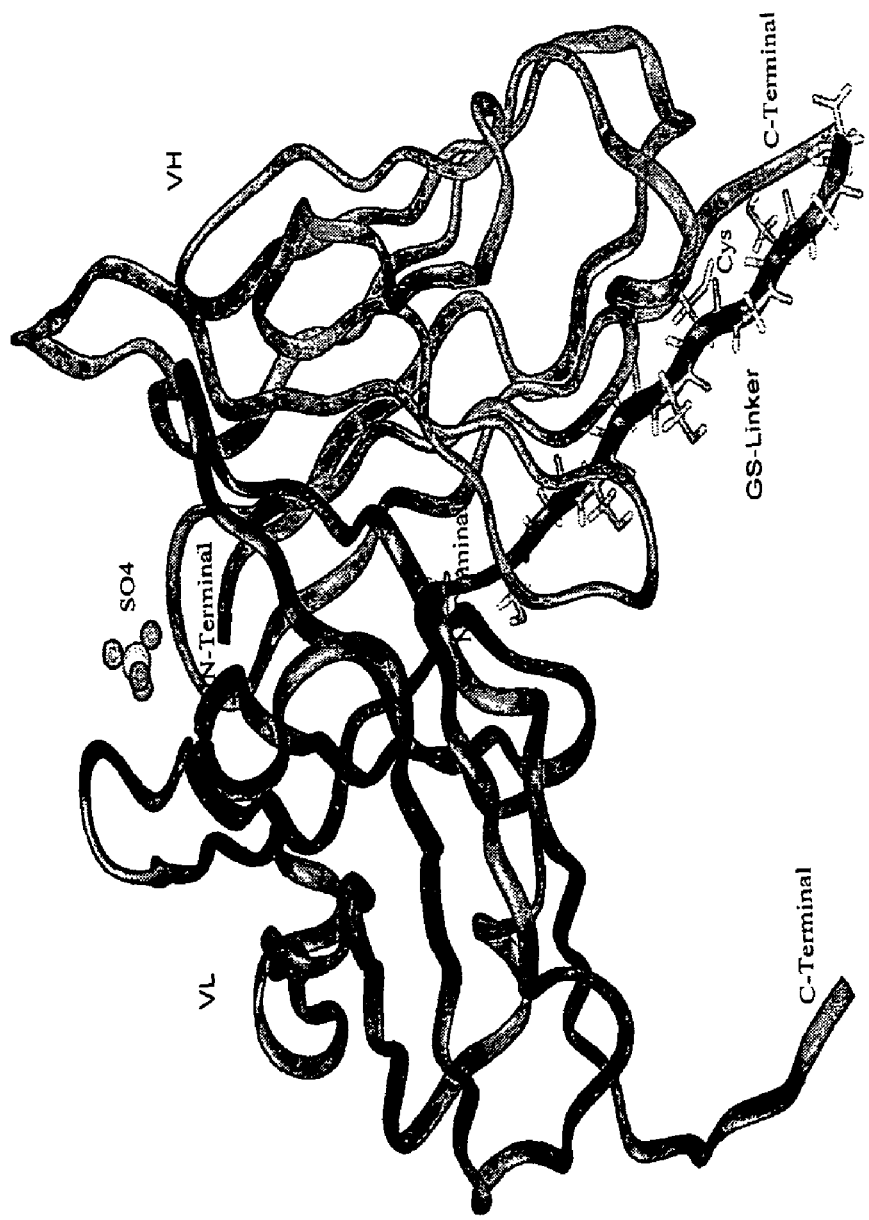
FIG. 5 shows the homology model of mouse anti-CEACAM6 $V_H$ and $V_L$ $S_CF_V$ chain built on the structural coordinates of 1MCP and containing a gly-ser linker (ggggsggggscggggs) (SEQ ID NO: 25) with a cysteine residue to attach other moieties, such as drugs.

A glycine-serine linker was constructed linking the VL C-terminus to VH N-terminus (distance≅33° A) with a cysteine residue in the following order (GS GSGS (cys) GSGSG). Referring to FIG. 5, the cysteine residue was introduced into the linker as it is a potential site for producing a drug-conjugated molecule.

The mouse CEACAM6 homology model and sequence was used to identify the best human acceptor for the VL and VH domains. The design was based on searching through the Kabat database (32) using the program fasta (33) with analysis of the modeled structure utilizing the program QUANTA (Accelrys, latest release 2000). Care was taken to conserve the canonical forms and residues at the interface between the light and heavy chains.

FIG. 6 shows Applicant's humanization of the VL chain of murine anti-CEACAM6. Sequences in grey comprise the complementarity determining regions (CDR 1, 2 and 3) which are identical to the acceptor human sequence. Residues in positions 1 and 53 in the framework regions will be mutated, as these are observed in humans and pack well against the CDRs. Referring now to FIG. 6, Applicant's light chain design was based on human sequence 163.15 (kabat database id 047292) (34). The first three residues of this sequence look like nonsense (possibly a result of the primer sequence), therefore, Applicant changed them to the most common residues found in human sequences (namely DIV). Applicant's first embodiment comprised a straight graft of the CEACAM6 CDRs into the human frameworks. In a second embodiment, Applicant changed the human Tyr at position 49 to the S found in the CEACAM6 light chain.

From the model, Ser49 is the most prominent framework residue in the binding site and binding affinity will be evaluated by mutation. The model shows that it might interact with M100a in the heavy chain CDR-H3. It also can interact with nearby CDR residues in the light chain. The N-terminus is occasionally important in binding antigen, hence Applicant's third embodiment changes the human Asp at position 1 to the Asn found in the CEACAM6 light chain. From the model, this Asn interacts with Pro95 in CDR-L3 and Lys27 in CDR-L1 and may also interact with Glu61 in CDR-H2. Applicant's third embodiment only has two backmutations.

FIG. 7 shows Applicant's humanization of the $V_H$ chain of murine anti-CEACAM6. Sequences in grey are the complementarity determining regions (CDR 1, 2 and 3) which are identical to the acceptor human sequence. Residues in positions 24, 37, 48 and 99 in the framework regions will be mutated as these are observed in humans and pack well against the CDRs.

For the heavy chain, Applicant searched the Kabat database (32) without success. Therefore, Applicant searched the NCBI non-redundant database. Once again, searching was done with fasta (33) with analysis of the modeled structure using the program QUANTA (Accelrys, latest release 2000). Care was taken to conserve the canonical forms and residues at the interface between the light and heavy chains. The heavy chain design was based on human sequence AAC51024 (NCBI accession 1791061) (35). It is notable that all three CDRs are the same length as murine CEACAM6.

These results demonstrate that the CDR-H3 loop might take the same conformation since sequence length is a better indicator of conformation than sequence composition. One embodiment of Applicant's composition comprises a straight graft of the CEACAM6 CDRs into these human frameworks. A second embodiment changes the human Ala at position 24 to the Thr found in the CEACAM6 heavy chain and similarly Val at position 48 to Ile.

Thr24 is a canonical residue for CDR-H1 and possibly interacts with Phe 27 and 29. I1e48 is a common back mutation in humanization experiments and from the model appears to support the conformation of CDR-H2. A third embodiment mutates the unusual Cys at position 93 to Ala and Val at position 37 to leucine. Leu37 is a residue at the light/heavy interface and will be kept murine. Cys93 in the model appears to be interacting with Tyr99. Cys93 may form a disulphide bridge with Cys102 in CDR-H3 (36), although this is appears unlikely from the model. Alternatively, Cys93 may comprise a metal binding site.

Gene Synthesis, Bacterial Expression and Protein Purification

Referring now to Table 2, below, Applicant utilized a gene synthesis approach to construct the murine ScFv and nine versions of VL-Glycine-Serine Linker-VH constructs of the humanized anti-CEACAM6 ScFv.

TABLE 2

Humanized ScFv Gene variables

| | | Light Chain | | Heavy Chain | | |
|---|---|---|---|---|---|---|
| Position | | 1 | 53 | 24 | 37 | 48 | 99 |
| Variable | 1 | D | Y | A | V | V | A |
| | 2 | D | Y | T | V | I | A |
| | 3 | D | Y | T | L | I | C |
| | 4 | D | S | A | V | V | A |
| | 5 | D | S | T | V | I | C |
| | 6 | D | S | T | L | I | C |
| | 7 | N | S | A | V | V | A |
| | 8 | N | S | T | V | I | C |
| | 9 | N | S | T | L | I | C |

Figure 8:
FIG. 8 shows Western blots for the murine $S_cF_v$ and humanized $S_cF_v$ version 8.

All ten constructs have been cloned into a pET19b N-terminally positioned histidine tagged vector. DNA sequencing has confirmed the authenticity of these constructs. Two of these constructs (murine ScFv and V.8 humanized ScFv) have been expressed in BL21 (DE3) PlysS competent bacteria with good protein expression and purified to >85% purity. The details of experimental procedure are described below. FIG. 8 shows the results of bacterial expression and purification on a Nickel affinity column of the murine ScFv and humanized ScFv version 6. The western blots were probed with an anti-histidine antibody (Qiagen). Expression time points are 0, 2 and 4 hours.

Bacterial Expression

Applicant has prepared the murine ScFv and 9 humanized ScFv variants as described above. These constructs were cloned into the pET19b vector as NcoI-BamH1 containing inserts which contain a 5' coding sequence for a hexa-histidine tag. DNA sequencing of all the constructs has shown authenticity of the inserts with the presence of an in-frame hexa-histidine tag placed N-terminal to the start site. Two of the ScFv's (murine ScFv and humanized ScFv V.8) have been successfully expressed in E. coli. The expressed recombinant proteins have been purified to ~85% purity using a $Ni^{2+}$ affinity chromatography column.

The DNA has been isolated from bacteria using the Qiagen Mini and Maxi preparation kits (Qiagen, CA). The sequence information, as DNA and amino acid sequences, is provided below:

Recombinant Protein Expression

Table 3 summarizes the steps of Applicant's method for recombinant protein expression.

TABLE 3

| | |
|---|---|
| 1 | Transform competent E. coli BL21 (DE3)PLysS cells (Invitrogen) with recombinant ScFv pET19b vector. Plate on LB agar ampicillin plates and grow overnight at 37° C. |
| 2 | Select a single colony and inoculate 20 ml of LB broth containing 100 µg/ml ampicillin and grow with vigorous shaking at 37° C. overnight. |
| 3 | Inoculate a 1 liter culture (LB, 100 µg/ml) 1:50 with non-induced overnight culture. Grow at 37° C. with vigorous shaking until an $OD_{600}$ of 0.6 is reached. |
| 4 | Take 1 ml sample prior to induction. |
| 5 | Induce expression by adding IPTG to a final concentration of 300 µM. |
| 6 | Incubate the culture for 4 hours at 37° C. Collect a second 1 ml sample. |
| 7 | Harvest cells by centrifugation at 4000 × g for 20 minutes. |
| 8 | Store pellet at −20° C. overnight or process immediately. |

Purification of Histidine Tagged Protein Under Denaturing Conditions

Thaw the cell pellet for 15 minutes on ice and resuspend in buffer (PBS, 8M urea, pH 8.0) at 5 ml per gram wet weight. Stir cells for 30-60 minutes at room temperature, then centrifuge lysate at 10,000×g for 20 minutes at room temperature and collect supernatant. Purification of histidine tagged proteins using Ni-NTA superflow (Qiagen) under denaturing conditions includes equilibration of the column with 5 column volumes of buffer 1 (100 mM $NaH_2PO_4$, 10 mM Tris-HCl, 8M urea, pH 8.0), apply lysate to column with a flow rate of 1 ml/min and wash with buffer 1 until the A280 is below 0.01 and then wash with buffer 2 (100 mM $NaH_2PO_4$, 10 mM Tris-HCl, 8M urea, pH 6.3) until the A280 is below 0.01. Finally the protein is eluted with buffer 3 (100 mM $NaH_2PO_4$, 10 mM Tris-HCl, 8M urea, pH 4.5).

Protein Refolding

Eluted protein is maintained at a low protein concentration (10-50 µg/ml). Four volumes of refolding buffer (20 mM Tris, 025 mM NaCl, 0.5% NP-40, 0.4 mM PMSF, 2 mM GSH, 0.2 mM GSSG, 100 mM EDTA, pH 7.8) are used to refolded at 4° C. for 24 hours. The refolded samples are dialyzed against 20 mM Tris-HCl, 120 MM NaCl, 5% Glycerol, pH 7.4) at 4° C. for 24 hours. Insoluble aggregates are removed by centrifugation. The samples are concentrated by lyophilization or by using an Amicon concentrator.

Protein Purification

The AKTA Prime (Amersham Bioscience) liquid chromatography protein purification system is used to further purify the recombinant proteins to >95% using, ion-exchange, hydrophobic and gel filtration columns sequentially. Since antibody fragments vary widely in surface composition and isoelectric points, there can be no generic purification schemes. A new procedure is designed for these antibody fragments. The protein purity can be analyzed using SDS-PAGE and silver staining.

As those skilled in the art will appreciate, it is desirable to produce a protein in the native state. The only case when alternative expression methods can become necessary is if native expression does not yield sufficient material for structure-function studies. Applicant has found that the murine ScFv and version 8 of the humanized ScFv are found in inclusion bodies. The recombinant protein was purified from these inclusion bodies and refolded to the native state. Fully functional molecules can then be obtained by further column purification steps (AKTA Prime, FPLC system) and assessed for activity by binding studies.

In certain embodiments, Applicant's method provides high level protein expression for the remaining 8 constructs based on the pET19b vector. In other embodiments, Applicant's method employs other vectors such as pET15 or 25 (Novagen) or pPROEX-Hta (Invitrogen) or pQE (Qiagen) or pGex-GST (Invitrogen).

In certain embodiments, bacterial expression provides functional molecules. In other embodiments, a baculovirus expression system is utilized. These embodiments include using the pFastBac vector (Invitrogen) or the pQE-TriSystem (Qiagen). The latter vector can be used for parallel protein expression using a single construct in *E. coli*, insect and mammalian cells. Generally, recombinant baculovirus can be generated by co-transfection of the shuttle vector and linearized baculovirus genomic DNA into insect cells such as Sf9 and Sf21 cells. Optimized protocols for co-transfection, virus amplification and plaque assay for virus titer determination will be obtained from the protocols of the different suppliers.

In yet other embodiments, Applicant uses the pQE-Trisystem (Qiagen) for expression in mammalian cells. This vector can be introduced into cells by traditional transfection techniques such as calcium phosphate, lipofection or electroporation. Protein expression is followed by western blotting with an anti-histidine antibody (Qiagen).

As those skilled in the art will appreciate, refolding of proteins can be a challenge, with many different techniques being available. In certain embodiments, Applicant uses a eukaryotic system as described above. Applicant has successfully refolded the murine and version 8 of the humanized ScFv with good solubility and functionality. Applicant's constructs can be evaluated for binding affinity utilizing the recombinant human CEACAM6 antigen, which has been cloned as a GST-tagged construct into the pGex vector (Invitrogen). DNA sequencing has confirmed the authenticity of the insert. As described above for the antibody fragments, human CEACAM6 antigen can be expressed in bacteria or baculovirus and purified to >95% purity using GST affinity chromatography in combination with AKTA Prime gel filtration chromatography.

Plates are coated overnight at 4° C. with an anti-histidine tagged antibody or anti-GST antibody in PBS/BSA. After washing the wells 4 times with PBS-Tween, purified histidine tagged ScFv or GST tagged CEACAM6 is added and incubated at room temperature for 2 hours. After washing in PBS-Tween 4 times CEACAM6 or ScFv is added, incubated for 1-2 hours at room temperature, washed and probed with an anti-GST antibody or anti-histidine antibody respectively. Secondary antibody is added in PBS/BSA and incubated at room temperature for 45 minutes. After washing 4 times in PBS-Tween, substrate solution (TMB) is added and color development is monitored in a microplate reader. These data are compared and contrasted to the original murine anti-CEACAM6 monoclonal antibody (murine IgG1 13.1).

The BIACore technology has become the standard method for measuring the affinity of antigen-antibody interactions and provides a tool to compare binding kinetics of a recombinant antibody fragment produced in bacteria with that of the parental monoclonal antibody. Applicant has discovered that the kinetic constants determined for the engineered monovalent antibody fragments are comparable to those obtained for the parental monovalent antibody fragments produced proteolytic cleavage from the parental monoclonal antibodies (35).

In real-time biomolecular interaction analysis (BIA), the antibody (ScFv or IgGl) is immobilized on a sensor chip surface, while a solution containing the antigen (CEACAM6) flows continuously over the surface or vice versa. Transport of the sample to the sensor surface is controlled with a microfluidics cartridge. A buffer solution is pumped at a constant flow rate over the sensor surface. A pulse of sample is injected and association of the analyte to the ligand is observed as an increase in the response expressed as resonance units (RU), followed as a function of time and presented as a sensorgram. From this data the association rate constant can be calculated. At the end of the injection, the sample is replaced by a continuous flow of buffer. The decrease in the response reflects the dissociation of the analyte from the ligand surface, and the data collected can be used to calculate the dissociation rate constant for the interaction.

In order to demonstrate that an anti-CEACAM6 monoclonal antibody can mediate pancreatic cancer cell killing Applicant has employed an in vitro cytotoxicity assay. This utilizes the CellTiter 96 Non-Radioactive Cell Proliferation Assay (Promega Corp., Madison, Wis.). Pancreatic cancer cell lines expressing CEACAM6 (CFPAC-1, ASPC-1, Capan-1, BXPC-3 and HPAF-2) are plated in 0.1 mL medium on day 0 in 96-well micro-titer plates (Falcon, #3072). On day 1, 10 µL of serial dilutions of the commercially available anti-CEACAM-6 Mab, the murine ScFv and nine versions of the humanized ScFv products will be added in replicates of 4 to the plates.

After incubation for 4 days at 37° C. in a humidified incubator, 20 µL, of a 20:1 mixture of [3-(4,5-dimethyl-2-yl)-5-(3-carboxymethoxyphenyl)-2-(4-sulfophenyl)-2H-tetrazolium, inner salt; MTS], 2 mg/ml, and an electron coupling reagent, phenazine methosulfate (PMS, 0.92 mg/ml in DPBS), are added to each well and incubated for 4 hours at 37° C. Absorbance is measured using Model 7520 microplate reader (Cambridge Technology, Inc.) at 490 nm. Data are expressed as the percentage of survival of control calculated from the absorbance corrected for background absorbance. The surviving fraction of cells will be determined by dividing the mean absorbance values of the monoclonal antibody by the mean absorbance values of the control.

Figure 9:
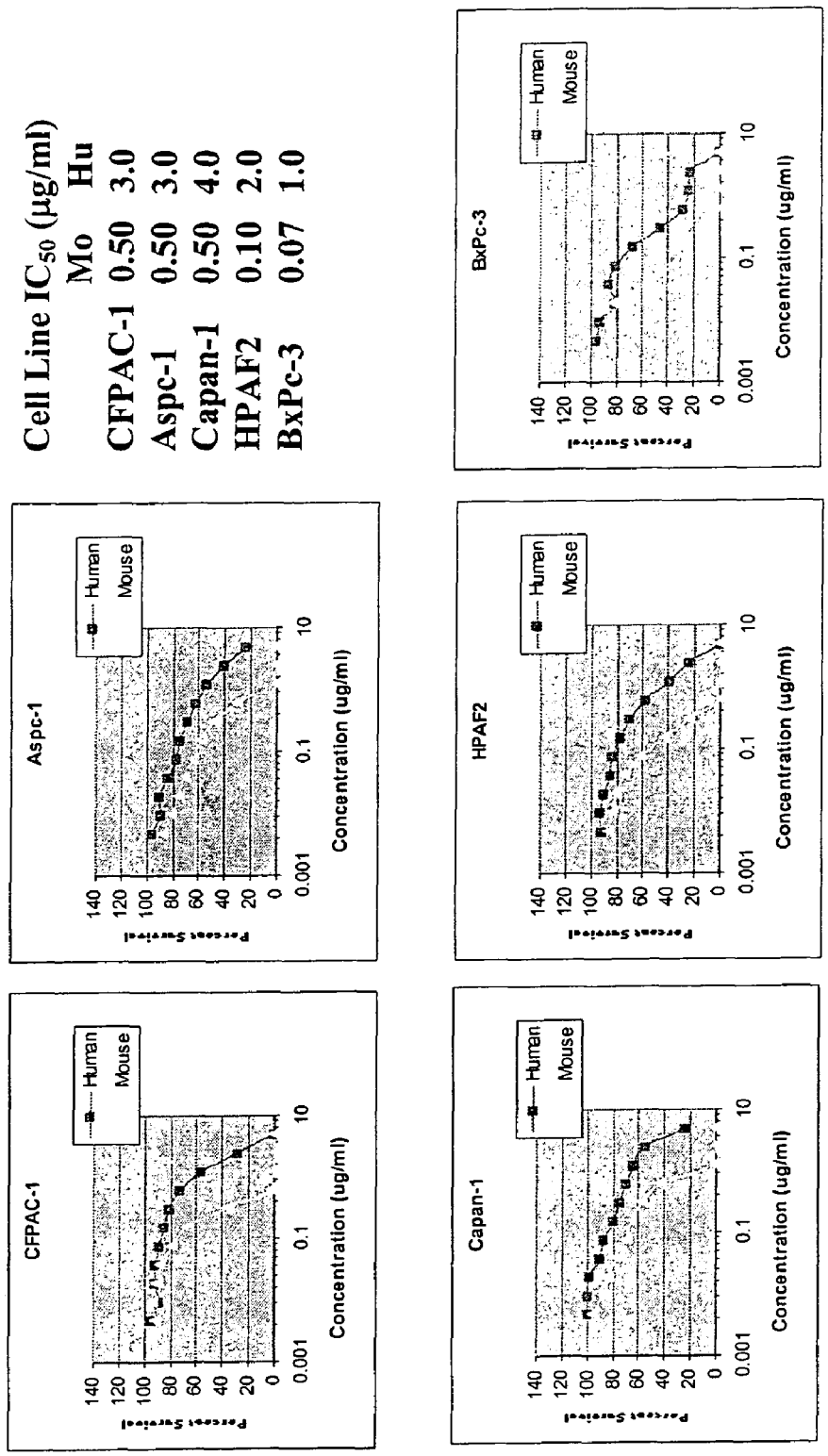
FIG. 9 demonstrates that the bacterially expressed mouse ScFv and humanized ScFv version 8 are active antibody fragments against CEACAM6 expressing pancreatic cancer cell lines. The data presented in the panels shows that the murine ScFv (yellow) and humanized ScFv (version 8) antibody fragments to CEACAM6 is efficient at cell killing in 5 different pancreatic cancer cell lines expressing CEACAM6. $IC_{50}$ values range from 0.07-4.0 µg/mL depending on the cell line.

As discussed above, we have bacterially expressed the original murine ScFv and humanized ScFv version 8, and we have now evaluated the efficacy of these antibody fragments in 5 different pancreatic cancer cell lines in culture. FIG. 9 demonstrates that the bacterially expressed mouse ScFv and humanized ScFv version 8 are active antibody fragments against CEACAM6 expressing pancreatic cancer cell lines.

Therapeutic Efficacy of the Mouse ScFv in a Mouse Model of Pancreatic Cancer

Figure 10:
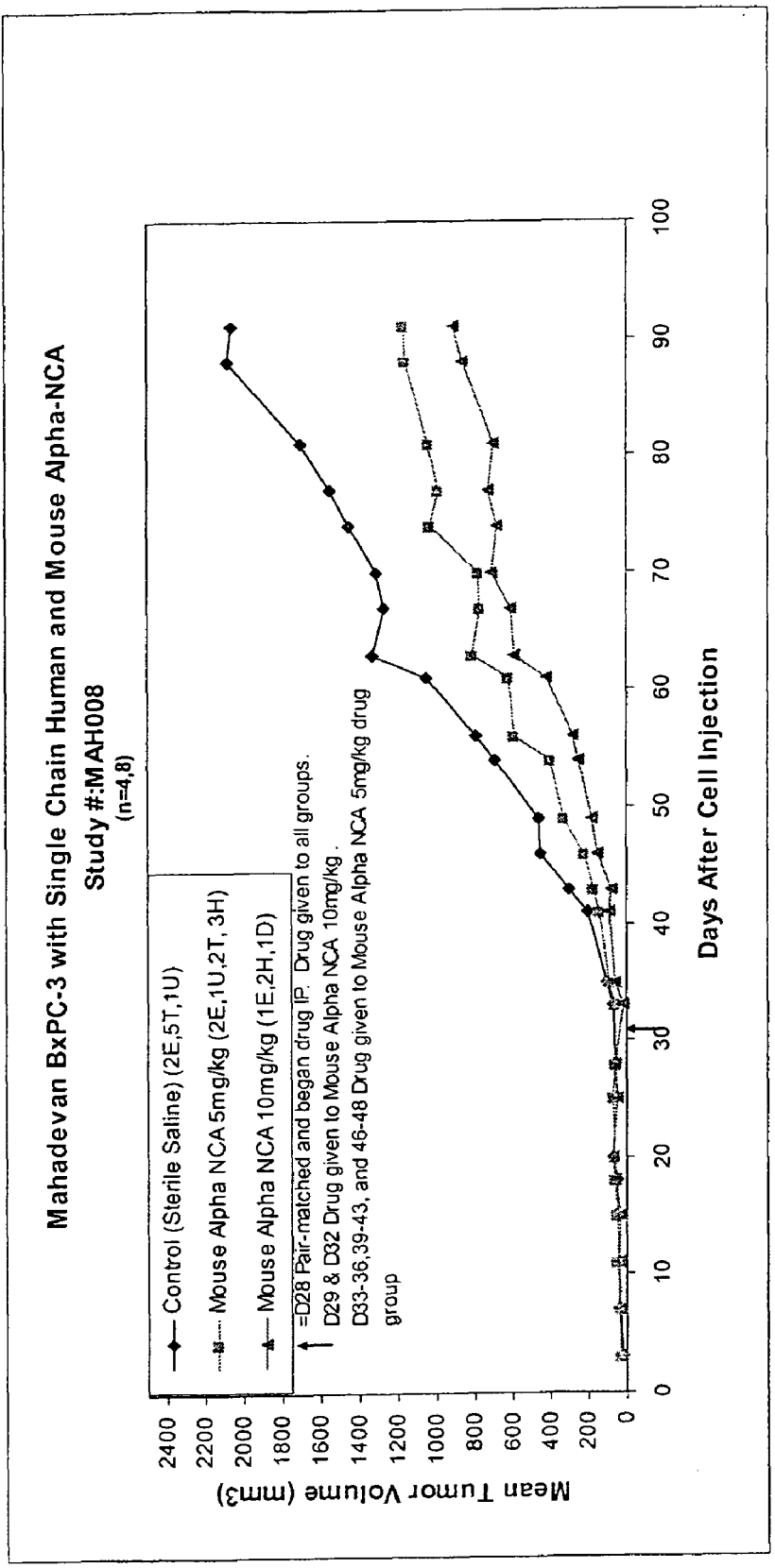
FIG. 10 shows that the murine ScFv antibody fragment given daily intraperitoneally is effective in reducing the tumor volume by 50-70% compared to the saline treated animals.

BXPC-3 pancreatic cancer cell line over-expressing CEACAM6 was utilized for this study. The mice were male athymic nude and were innoculated with 10 million cells in the flank region. Tumors were grown to a mean volume of 50 mm³. There were 8 mice in the control and 8 mice in the treated groups. Treatment was initiated at day 28 after innoculation with recombinant mouse ScFv at 5 mg/kg or 10 mg/kg given intraperitoneally daily for 2 weeks. Tumor volumes were measured weekly. All animals maintained their weights in both groups. The data demonstrate that there was a 50-70% reduction in tumor volume with treatment compared to the untreated animals (FIG. 10).

Treatment of HPAF-2 Cells with Anti-CEACAM6 Mab Promotes Apoptosis

In order to ascertain the mechanism(s) of anti-CEACAM6 monoclonal antibody (Mab) mediated apoptosis, a gene expression profile (GEP) study was performed utilizing the human affymetrix U133A oligonucleotide gene array consisting of ~22,000 probes. HPAF-2 pancreatic cancer cells were treated with 1 µg/mL anti-CEACAM6 Mab for 6 and 24 hours. The control was untreated HPAP-2 cells. Total RNA was extracted utilizing the RNeasy Mini Kit (Qiagen, CA) according to the manufacturer's instructions. The amount of total RNA isolated from the cells was quantified using spectrophotometric $OD_{260}$ measurements with yields ≧25 µg/sample. 5 µg of mRNA was used to generate first-strand cDNA by using a T7-linked oligo (dT) primer. After second-strand synthesis, in vitro transcription (Ambion) was performed with biotinylated UTP and CTP (Enzo Diagnostics), resulting in 40- to 80-fold linear amplification of RNA. 40 µg of biotinylated RNA was fragmented to 50- to 150-nt size before overnight hybridization at 45° C. to HG-U133A 2.0 Affymetrix array (Santa Clara, Calif.). Each gene on this chip is represented by 10 to 20 oligonucleotides, termed a 'probe set'. The intensity of hybridization of labeled mRNA to these sets reflects the level of expression of a particular gene. After washing, arrays were stained with streptavidin-phycoerythrin (Molecular Probes) and scanned on a Hewlett-Packard scanner. Intensity for each feature of the array was captured by using GENECHIP SOFTWARE (Affymetrix, CA), and a single raw expression level for each gene was derived from the 10-20 probe pairs representing each gene by using a trimmed mean algorithm. Intensity values were scaled such that overall intensity for each chip of the same type was equivalent. The mean (±SD) difference between the scaling factors of all GeneChips was 0.75±0.15. The ratio of GAPDH 3' to 5' (1.02±0.10) indicated a high overall quality of the samples. Well measured genes were defined genes that had a ratio of signal intensity to background noise of greater than 2 in more than 80% of the samples hybridized. Mab treated was compared to the control sample and lists of 'robust increasers' or 'robust decreasers' were generated utilizing the Affymetrix Data Analysis Program (Affymetrix MAS 5.0). Fundamentals' guide was used to import these lists into GeneSpring (version 5.0) and obtain the intersection of robust increasers or decreasers respectively. Gene expression profiles were further classified according genes involved in promoting and evading apoptosis and self-sufficiency in growth signals including oncogenes and insensitivities to growth inhibitory signals.

The results indicated that several apoptotic proteins were robustly up-regulated at 6 hours and 24 hours respectively. The apoptotic protein that was markedly over-expressed at 6 hours was caspase-2 (~10-fold) compared to untreated HPAF-2 cells. However, at 24 hours caspase-2 levels had decreased to ~4-fold compared to untreated HPAF-2 cells. This result was confirmed with a western blot analysis after treating HPAF-2 cells with anti-CEACAM6 Mab at 1 µg/mL for 6, 24, 48 and 72 hours with a rabbit polyclonal antibody to active caspase-2 (Abcam Inc, MA) which migrates at 34 kDa (FIG. 11). There appears to be a basal level of caspase-2 in untreated cells (also observed in the gene expression profile analysis) and at 6 hours after treatment with anti-CEACAM6 Mab the level of caspase-2 increases and remains elevated for 48 hours. However, as cells undergo apoptosis the level decreases to below basal level. It has been difficult to assign caspase-2 to the effector or initiator caspase groups. It bears sequence homology to initiators (caspase-9 and CED-3), but its cleavage specificity is closer to the effectors (caspase-3 and -7). It has been observed that cell death occurring during the metaphase/anaphase transition is characterized by the activation of caspase-2 (which can be activated in response to DNA damage) and/or mitochondrial membrane permeabilization with the release of cell death effectors such as apoptosis-inducing factor and the caspase-9 and -3 activator cytochrome c (28). Although the mode of activation of caspase-2 is yet to be determined caspase-2 plays critical and singular roles in the control of programmed cell death.

Diagnostic and Prognostic Marker

The anti-CEACAM6 monoclonal antibody has not been developed as a diagnostic and/or prognostic marker. An immunohistochemical analysis on tissue microarrays from 243 colorectal patient biopsies prior to adjuvant chemotherapy from a randomized controlled clinical trial demonstrated that CEACAM6 over-expression independently predicted for poor overall survival in comparison to CEA or CEACAM1. In this tissue array CEACAM6 over-expression was present 55% of patients (Jantscheff P, Terracciano L, Lowy A. et al. Expression of CEACAM6 in resectable colorectal cancer: a factor of independent prognostic significance. *J. Clin. Oncol.* 2003, 21(19): 3638-46), validating it as a clinical marker and a potential therapeutic target in colorectal cancer. We also analyzed 30 patients with pancreatic cancer and found >75% to have CEACAM6 present on their tumors. Therefore the mouse or the humanized monoclonal antibody and/or the antibody fragments (ScFv) will be useful as a diagnostic and prognostic marker in any cancer or hematological malignancy that over-expresses (by greater than 2-fold compared to normal counterparts) CEACAM6.

While the preferred embodiments of the present-invention have been illustrated in detail, it should be apparent that modifications and adaptations to those embodiments may occur to one skilled in the art without departing from the scope of the present invention.

Obviously, numerous modifications and variations of the present invention are possible in light of the above teachings. It is therefore to be understood that within the scope of the appended claims, the invention may be practiced otherwise than as specifically described herein

REFERENCES

1. Von Hoff, D D, Mahadevan, D, Bearss, D J. New Developments in the Treatment of Patients with Pancreatic Cancer. *Clinical Oncology Updates,* 2001, 4: 1-15.
2. Lynch H T, Smyrk T, Kern S E, Hruban R H, Lightdale C J, Lemon S J, Lynch J F, Fusaro L R, Fusaro R M, Ghadirian P. Familial pancreatic cancer. *Semin Oncol.* 1996, 23(2): 251-75.
3. Jaffee E M, Hruban R H, Canto M, Kern S E. Focus on pancreas cancer. *Cancer Cell.* 2002, 2(1):25-8.
4. Bardeesy N, DePinho R A. Pancreatic cancer biology and genetics. *Nat Rev Cancer,* 2002, 2(12):897-909.
5. Cubilla A L, Fitzgerald P J. Morphological patterns of primary nonendocrine human pancreas carcinoma. *Cancer Res.* 1975, 35(8):2234-48.
6. Klein W M, Hruban R H, Klein-Szanto A J, Wilentz R E. Direct correlation between proliferative activity and dysplasia in pancreatic intraepithelial neoplasia (PanIN): addi- 6. tional evidence for a recently proposed model of progression. *Mod Pathol.* 2002, 15(4):441-7.
7. Solcia, E, Capela, C, Kloppel, G. Tumors of the Pancreas (Ed. Rosai J.) (Armed Forces Institute of Pathology, Washington D.C., 1995).
8. Iacobuzio-Donahue C A, Ryu B, Hruban R H, Kern S E. Exploring the host desmoplastic response to pancreatic carcinoma: gene expression of stromal and neoplastic cells at the site of primary invasion. *Am J Pathol.* 2002, 160(1): 91=9.
9. Lohr M, Schmidt C, Ringel J, Kluth M, Muller P, Nizze H, Jesnowski R. Transforming growth factor-beta1 induces desmoplasia in an experimental model of human pancreatic carcinoma. *Cancer Res.* 2001, 61(2):550-5.
10. Holloway S, Davis M, Jaber R, Fleming J. A Clinically Relevant Model of Human Pancreatic Adenocarcinoma Identifies Patterns of Metastasis Associated with Alterations of the TGF-beta/Smad4 Signaling Pathway. *Int J Gastrointest Cancer.* 2003, 33(1):61-70.
11. Han H, Bearss D J, Browne L W, Calaluce R, Nagle R B, Von Hoff D D. Identification of differentially expressed genes in pancreatic cancer cells using cDNA microarray. *Cancer Res.* 2002, 62(10):2890-6.
12. Gardner-Thorpe J, Ito H, Ashley S W, Whang E E. Differential display of expressed genes in pancreatic cancer cells. *Biochem Biophys Res Commun.* 2002, 293(1):391-5.
13. Friess H, Ding J, Kleeff J, Fenkell L, Rosinski J A, Guweidhi A, Reidhaar-Olson J F, Korc M, Hammer J, Buchler M W. Micro array-based identification of differentially expressed growth- and metastasis-associated genes in pancreatic cancer. *Cell Mol Life Sci.* 2003, 60(6): 1180-99.
14. Ryu B, Jones J, Blades N J, Parmigiani G, Hollingsworth M A, Hruban R H, Kern S E. Relationships and differentially expressed genes among pancreatic cancers examined by large-scale serial analysis of gene expression. *Cancer Res.* 2002, 62(3):819-26.
15. Iacobuzio-Donahue C A, Maitra A, Olsen M, Lowe A W, van Heek N T, Rosty C, Walter K, Sato N, Parker A, Ashfaq R, Jaffee E, Ryu B, Jones J, Eshleman J R, Yeo C J, Cameron J L, Kern S E, Hruban R H, Brown P O, Goggins M. Exploration of global gene expression patterns in pancreatic adenocarcinoma using cDNA microarrays. *Am J Pathol.* 2003, 162(4):1151-62.
16. Smit V T, Boot A J, Sinits A M, Fleuren G J, Cornelisse C J, Bos J L. KRAS codon 12 mutations occur very frequently in pancreatic adenocarcinomas. *Nucleic Acids Res.* 1988, 16(16):7773-82.
17. Griffin C A, Hruban R H, Morsberger L A, Ellingham T, Long P P, Jaffee E M, Hauda K M, Bohlander S K, Yeo C J. Consistent chromosome abnormalities in adenocarcinoma of the pancreas. *Cancer Res.* 1995, 55(11):2394-9.
18. Aoki K, Yoshida N, Matsumoto H, Ide T, Sugimura M, Terada A. Suppression of Ki-ras p21 levels leading to growth inhibition of pancreatic cancer cell lines with Ki-ras mutation but not those without Ki-ras mutation. *Mol. Carcinog.* 1997, 20: 251-258.
19. Ikeda N, Nakajima Y, Sho M, Adachi M, Huang C L; Iki K, Kanehiro H, Hisanaga M, Nakano H; Miyake M. The association of K-ras gene mutation and vascular endothelial growth factor gene expression in pancreatic carcinoma. *Cancer.* 2001, 92(3):488-99.
20. Wagner M, et al. A murine tumor progression model for pancreatic cancer recapitulating the genetic alterations of the human disease. *Genes Dev.* 2001, 15:286-293.
21. Sotillo R. et al. Wide spread tumors in knock-in mice carrying a CDK4 protein insensitive to INK4 inhibitors. *EMBO J.* 2001, 20:6637-6647.
22. Lersch C, et al. Randomized phase II study of SCH66336 and gemcitabine in the treatment of metastatic adenocarcinoma of the pancreas. *Proc. Am. Soc. Clin. Oncol.* 2001, Abstract 608.
23. Beauchemin N, Draber P, Dveksler G, Gold P, Gray-Owen S, Grunert F, Hammarstrom S, Holmes K V, Karlsson A, Kuroki M, Lin S H, Lucka L, Najjar S M, Neumaier M, Obrink B, Shively J E, Skubitz K M, Stanners C P, Thomas P, Thompson J A, Virji M, von Kleist S, Wagener C, Watt S, Zimmermann W. Redefined nomenclature for members of the carcinoembryonic antigen family. *Exp Cell Res.* 1999, 252(2):243-9.
24. Kuroki M, Abe H, Imakiirei T, Liao S, Uchida H, Yamauchi Y, Oikawa S, Kuroki M. Identification and comparison of residues critical for cell-adhesion activities of two neutrophil CD66 antigens, CEACAM6 and CEACAM8. *J. Leukoc Biol.* 2001, 70(4):543-50.
25. Chevinsky A H. CEA in tumors of other than colorectal origin. *Semin Surg Oncol.* 1991, 7(3):162-6.
26. Scholzel S, Zimmermann W, Schwarzkopf G, Grunert F, Rogaczewski B, Thompson J. Carcinoembryonic antigen family members CEACAM6 and CEACAM7 are differentially expressed in normal tissues and oppositely deregulated in hyperplastic colorectal polyps and early adenomas. *Am J Pathol.* 2000, 156(2):595-605.
27. Ordonez C, Screaton R A, Ilantzis C, Stanners C P. Human carcinoembryonic antigen functions as a general inhibitor of anoikis. *Cancer Res.* 2000, 60(13):3419-24.
28. Sippel C J, Fallon R J, Perlmutter D H. Bile acid efflux mediated by the rat liver canalicular bile acid transport/ecto-ATPase protein requires serine 503 phosphorylation and is regulated by tyrosine 488 phosphorylation. *J Biol Chem.* 1994, 269(30):19539-45.
29. Brummer J, Neumaier M, Gopfert C, Wagener C. Association of pp60c-src with biliary glycoprotein (CD66a), an adhesion molecule of the carcinoembryonic antigen family downregulated in colorectal carcinomas. *Oncogene.* 1995, 11(8):1649-55.
30. Beauchemin N, Kunath T, Robitaille J, Chow B, Turbide C, Daniels E, Veillette A. Association of biliary glycoprotein with protein tyrosine phosphatase SHP-1 in malignant colon epithelial cells. *Oncogene.* 1997, 14(7):783-90.
31. Satow Y, Cohen G H, Padlan E A, Davies D R. Phosphocholine binding immunoglobulin Fab McPC603. An X-ray diffraction study at 2.7 A. *J Mol Biol.* 1986, 190(4):593-604.
32. Johnson G, Wu T T. Kabat Database and its applications: future directions. *Nucleic Acids Res.* 2001, 29(1):205-6.
33. Pearson W R. Flexible sequence similarity searching with the FASTA3 program package. *Methods Mol Biol.* 2000; 132:185-219.
34. Coomber D W, Hawkins N J, Clark M A, Ward R L. Generation of anti-p53 Fab fragments from individuals with colorectal cancer using phage display. *J Immunol.* 1999, 163(4):2276-83.
35. Glas A M, Nottenburg C, Milner E C. Analysis of rearranged immunoglobulin heavy chain variable region genes obtained from a bone marrow transplant (BMT) recipient. *Clin Exp Immunol.* 1997, 107(2):372-80.
36. Akashi S, Kato K, Torizawa T, Dohmae N, Yamaguchi H, Kamachi M, Harada A, Imanaka T, Shimada I, Takio K. Structural characterization of mouse monoclonal antibody 13-1 against a porphyrin derivative: Identification of a disulfide bond in CDR-H3 of Mab 13-1. *Biochem Biophys Res Commun*. 1997, 240(3):566-72.
37. Pluckthun A, Krebber A, Krebber C, Horn, U, Knupfer U, Wenderoth R, Nieba L, Proba K, and Riesenberg D. Producing antibodies in *Escherichia coli*: from PCR to fermentation. In: Antibody Engineering, McCafferty J, Hoogenboom R, and Chiswell D J, Eds. (IRL Press, Oxford; 1996, 203-252).
38. Alfthan K. Surface plasmon resonance biosensors as a tool in antibody engineering. *Biosens Bioelectron*. 1998, 13(6):653-63.
39. Issaq H J, Veenstra T D, Conrads T P, Felschow D. The SELDI-TOF MS approach to proteomics: protein profiling and biomarker identification. *Biochem Biophys Res Commun*. 2002, 292(3):587-92.
40. Bruns C J, Harbison M T, Davis D W, Portera C A, Tsan R, McConkey D J, Evans D B, Abbruzzese J L, Hicklin D J, Radinsky R. Epidermal growth factor receptor blockade with C225 plus gemcitabine results in regression of human pancreatic carcinoma growing orthotopically in nude mice by antiangiogenic mechanisms. *Clin Cancer Res*. 2000; 6(5):1936-48.
41. Kaufmann M, Lindner P, Honegger A, Blank K, Tschopp M, Capitani G, Pluckthun A, Grutter M G. Crystal structure of the anti-His tag antibody 3D5 single-chain fragment complexed to its antigen. *J Mol Biol*. 2002, 318(1):135-47.
42. Islam S A, Carvin D, Sternberg M J, Blundell T L. HAD, a data bank of heavy-atom binding sites in protein crystals: a resource for use in multiple isomorphous replacement and anomalous scattering. *Acta Crystallogr D Biol Crystallogr*. 1998, 54(Pt 6 Pt 1): 1199-206.
43. Hallborn J, Carlsson R. Automated screening procedure for high-throughput generation of antibody fragments. *Biotechniques*. 2002, Suppl:30-7.

The invention claimed is:

1. A method of treating pancreatic cancer, gastrointestinal cancer, lung cancer, breast cancer, cervical cancer, uterine cancer, ovarian cancers, colorectal cancer, and/or stomach cancer, comprising administering an effective amount of an anti-CEACAM6 antibody or antibody fragment thereof comprising all six of the CDRs of monoclonal antibody 13.1 to a patient with pancreatic cancer, gastrointestinal cancer, lung cancer, breast cancer, cervical cancer, uterine cancer, ovarian cancers, colorectal cancer, and/or stomach cancer, wherein the antibody or antibody fragment induces apoptosis in cancer cells.

2. The method of claim 1, wherein the antibody or antibody fragment thereof induces apoptosis against cancer cells in the Cellular Cytotoxicity Assay described herein.

3. The method of claim 1, which is a method of treating pancreatic cancer.

4. The method of claim 1, which is a method of treating gastrointestinal cancer.

5. The method of claim 1, which is a method of treating lung cancer.

6. The method of claim 1, which is a method of treating breast cancer.

7. The method of claim 1, which is a method of treating cervical cancer.

8. The method of claim 1, which is a method of treating uterine cancer.

9. The method of claim 1, which is a method of treating ovarian cancers.

10. The method of claim 1, which is a method of treating colorectal cancer.

11. The method of claim 1, which is a method of treating stomach cancer.

12. The method of claim 1, wherein the antibody or antibody fragment thereof is humanized.

13. The method of claim 1, wherein the antibody or antibody fragment thereof is chimeric.

14. The method of claim 1, wherein said antibody or antibody fragment thereof is an antibody fragment, and the antibody fragment is an ScFv.

15. The method of claim 14, wherein the ScFv is murine or humanized.

16. The method of claim 1, wherein the patient is a human or a non-human animal.

17. The method of claim 1, wherein the patient is a human.

18. The method of claim 17, wherein the antibody or antibody fragment thereof is administered parenterally, intraperitoneally, intravenously, subcutaneously, orally, nasally, via inhalation or rectally.

19. The method of claim 1, wherein the antibody or antibody fragment thereof is administered intravenously at a dosage of from 5 mg/m$^2$ to 2000 mg/m$^2$.

20. The method of claim 1, wherein the antibody is monoclonal antibody 13.1.

* * * * *